United States Patent [19]
Longo et al.

[11] Patent Number: 5,958,875
[45] Date of Patent: Sep. 28, 1999

[54] SYNTHETIC PEPTIDES DERIVATIVES WITH NERVE GROWTH FACTOR-LIKE NEUROTROPHIC ACTIVITY

[75] Inventors: Frank M. Longo, San Francisco; Marston Manthorpe, San Diego, both of Calif.

[73] Assignee: The Regents of the University of California, Oakland, Calif.

[21] Appl. No.: 08/623,690

[22] Filed: Mar. 29, 1996

[51] Int. Cl.⁶ .............................. A61K 38/12; C07K 5/12
[52] U.S. Cl. ................................ 514/11; 514/13; 514/14; 514/15; 514/16; 514/17; 530/326; 530/327; 530/328; 530/329; 530/330
[58] Field of Search ..................................... 530/326–330, 530/317; 514/11, 13–17

[56] References Cited

U.S. PATENT DOCUMENTS

| | | | |
|---|---|---|---|
| 5,134,121 | 7/1992 | Mobley et al. | 514/14 |
| 5,229,500 | 7/1993 | Barde et al. | 530/399 |
| 5,236,898 | 8/1993 | Krstenansky et al. | 514/9 |
| 5,349,055 | 9/1994 | Persson et al. | 530/399 |

FOREIGN PATENT DOCUMENTS

| | | |
|---|---|---|
| 0 418 590 A1 | 8/1990 | European Pat. Off. . |
| 0 476 933 A1 | 3/1992 | European Pat. Off. . |
| WO 90/10644 | 9/1990 | WIPO . |
| WO 93/03140 | 5/1992 | WIPO . |
| WO 93/19088 | 2/1993 | WIPO . |
| WO 94/12539 | 11/1993 | WIPO . |
| 9521193 | 8/1995 | WIPO . |

OTHER PUBLICATIONS

F.M. Longo, M. Manthorpe, Y. Xie, and S. Varon, Synthetic NGF Peptide Derivatives Prevent Neuronal Death Via a p75 Receptor–Dependent Mechanism, *Journal of Neuroscience Research*, 48:1–17 (1997).

Y.M. Xie and F.M. Longo, Neurotrophic Activity of Synthetic Peptide Derivatives Corresponding to NGF Loop Region 92–98, *Society for Neurosciences 1997 Annual Meeting* (Oct. 25–30, 1997).

Angeletti et al., "Subunit structure and amino acid composition of mouse submaxillary gland nerve growth factor", *Biochem.* 10:463–469 (1971).

Bay et al., "Assessment of neurotrophic activity of a broad spectrum of pharmacologic agents in PC12 cells", *Soc. Neurosci. Abst.* 16:995 (1990).

Friden et al., "Blood–brain barrier penetration and in vivo activity of an NGF conjugate", *Science,* 259:373–377 (1993).

Ibanez et al., "Disruption of the low affinity receptor–binding site in NGF allows neuronal survival and differentiation by binding to the trk gene product" *Cell* 69:329–341 (1992).

Ibanez et al., "Chimeric molecules with multiple neurotrophic activities reveal structural elements determining the specificities of NGF and BDNF", *EMBO J.* 10:2105–2110 (1991).

Ibanez et al., "An extended surface of binding to Trk tyrosine kinase receptors in NGF and BDNF allows the engineering of a multifunctional pan–neurotrophin", *EMBO J.* 12:2281–2293 (1993).

Ilag et al., "Role of variable β–hairpin loop in determining biological specificities in neurotrophin family", *J. Biol. Chem.* 269:19941–19946 (1994).

Lehmann et al., "Neurite outgrowth of neurons of rat dorsal root ganglia induced by new neurotrophic substances with guanidine group." *Neurosci. Lett.* 152:57–60 (1993).

L LeSauteur, L. Wei, B.F. Gibbs, and H.U. Saragovi; "Small Peptide Mimics of Nerve Growth Factor Bind TrkA Receptors and Affect Biological Responses"; The *Journal of Biological Chemistry,* 270:6564–6569, (1995).

Longo et al., "The in vitro biological effect of nerve growth factor is inhibited by synthetic peptides", *Cell Regulation* 1:189–195 (1990).

McDonald and Chao, "Structural determinants of neurotrophic action", *J. Biol. Chem.* 270:19669–19672 (1995).

Murphy et al., "Immunological relationships of NGF, BDNF, and NT–3: Recognition and functional inhibition by antibodies to NGF", *J. Neurosci.,* 13:2853–2862 (1993).

K. Rashid, C.E.E.M. Van der Zee, G.M. Ross, C.A. Chapman, R.J. Racine, R. J. Riopelle, and M. Fahnestock; *24th Ann. Mtg. Soc. Neurosci.,*20:1–2 Abstract 289.3 (1994).

Ross et al., "NGF/BDNF Chimeric Proteins: Analysis of Neurotrophin Specificity by Homolog–scanning Mutagenesis", *Soc. for Neurosci. Abstr.,* v 20(1–2) p. 678, Abstr. 289.2 and 289.3 (1994).

*Primary Examiner*—Cecilia J. Tsang
*Assistant Examiner*—Bennett Celsa
*Attorney, Agent, or Firm*—Townsend & Townsend & Crew LLP

[57] ABSTRACT

This invention provides compounds displaying NGF agonist activity, wherein the compounds comprise a multimer of a sequence of amino acid residues or biologically functional equivalents thereof, the sequence being substantially homologous to residues 29–38 of NGF, residues 43–47 of NGF or residues 92–97 of NGF. Preferably, the multimer is a cyclic dimer wherein the monomeric amino acid sequences are linked to each other by disulfide bridges. This invention also provides methods and compositions for the treatment of disorders involving NGF-responsive cells, by administering an effective amount of the multimeric NGF agonists of this invention to an individual suffering from such disorder.

14 Claims, 10 Drawing Sheets

| Peptide | | HPLC fxn with highest activity | % NGF max | Peptide conc. with max. activity |
|---|---|---|---|---|
| P7: | IPenKGKEVCT-NH$_2$ | 5th of 5 | 75 | 250 μM |
| P8: | DPenIKGKEVCT-NH$_2$ | 3rd of 3 | 40 | 500 μM |
| P9: | DPenIKGKEVTCV-NH$_2$ | 3rd of 3 | 50 | 300 μM |
| P10: | TPenDIKGKEVTCV-NH$_2$ | 6th of 7 | 30 | 2000 μM |
| P11: | TPenTDIKGKEVTCV-NH$_2$ | 5th of 5 | 55 | 1000 μM |
| 7P: | ICKGKEVPenT-NH$_2$ | 4th of 4 | 55 | 500 μM |
| 8P: | DCIKGKEVPenT-NH$_2$ | 5th of 5 | 10 | 1000 μM |
| 9P: | DCIKGKEVTPenV-NH$_2$ | 1st of 1 | 10 | 2000 μM |
| 10P: | TCDIKGKEVTPenV-NH$_2$ | 3rd of 4 | 30 | 1000 μM |
| 11P: | ACTDIKGKEVTPenV-NH$_2$ | 3rd of 3 | 45 | 500 μM |

FIG. 3

```
            Mbzl  2chloroZ        2chloroZ  Bzl             Mbzl    Bzl
            (138)  (187)           (187)   (108)            (138)  (108)
             |      |                |       |                |      |
    P7:    I Pen    K       G        K       E       V        C      T  - NH2
             └──────────────────────────────────────────────────┘
```

SYNTHETIC PEPTIDES DERIVATIVES WITH NERVE GROWTH FACTOR-LIKE NEUROTROPHIC ACTIVITY

BACKGROUND OF THE INVENTION

This invention relates to neurotrophic factors and their involvement in neurodegenerative and other neuropathic disorders. More particularly, this invention relates to analogs of nerve growth factor.

1. Field of the Invention

Nerve growth factor (NGF) and other growth factors act via cell surface receptors to prevent neuronal death in the contexts of neural development, neurodegenerative disease, ischemia, axotomy and excessive excitatory amino acids (reviewed in: Longo et al., Nerve Growth Factor actions in the PNS and CNS. Eds: S. E. Loughlin and J. H. Fallon, Academic Press; pp 209–256 (1993)). They also promote neural regeneration and enhance neuronal function. The sequence of murine NGF and human NGF is reported in Ullrich et al. Nature 303:821–825 (1983).

Therapeutic applications of native neurotrophic factors have been limited by poor ligand penetration of the blood-nerve barrier, blood-brain barrier and CNS parenchyma, ligand stability and receptor specificity, attributable in part to the size of the native factors (Friden et al., "Blood-brain barrier penetration and in vivo activity of an NGF conjugate", Science, 259:373–377 (1993)). One approach for overcoming these limitations consists of development of low molecular weight, stable agonists or partial agonists capable of mimicking specific activities of native neurotrophic factor ligands.

Very few agents have been discovered which mimic both the survival- and neurite-promoting neurotrophic activity of NGF. Phorbol esters mimic NGF and ciliary neurotrophic factor (CNTF) neurotrophic activity presumably by influencing protein kinase C signal transduction (Montz et al., "Tumor-promoting phorbol diester mimics two distinct neuronotrophic factors", Dev. Brain Res, 23:150–154 (1985)). Gangliosides and several structurally unrelated lipids and detergents promoted survival and neurite outgrowth of dissociated sympathetic, ciliary and dorsal root ganglion (DRG) neurons and survival of PC12 cells, although this activity was unlikely to be mediated by specific NGF receptor interactions (Ferrari et al., "Gangliosides rescue neuronal cells from death after trophic factor deprivation", J. Neurosci. 13: 1879–1887 (1985)). Bay et al. ("Assessment of neurotrophic activity of a broad spectrum of pharmacologic agents in PC12 cells", Soc. Neurosci. Abst. 16:995 (1990)), assessed 65 synthetic and naturally occurring compounds for NGF-like neurotrophic activity with PC12 cells and found that, except for other growth factors, only cyclic AMP analogs had trophic activity. Triap (1,1,3 tricyano-2-amino-1-propene) is a small molecule which promoted survival and neurite outgrowth of cultured sympathetic ganglion neurons and PC12 cells (Paul et al., "1,1,3 tricyano-2-amino-1-propene (Triap) stimulates choline acetyltransferase activity in vitro and in vivo." Dev. Brain Res. 67:113–120 (1992)). The observations that Triap maximally induced ChAT enzyme activity at concentrations that did not affect neuronal morphology and that Triap was synergistic rather than additive to NGF in promoting ChAT activity led these investigators to suggest that Triap did not act through NGF receptors. Lehmann et al., ("Neurite outgrowth of neurons of rat dorsal root ganglia induced by new neurotrophic substances with guanidine group." Neurosci. Lett. 152:57–60 (1993)), reported that two of 19 compounds related to isaxonine (2-isopropylamino-pyrimidine) were particularly effective in promoting neurite outgrowth from DRG explants. That these compounds acted by mechanisms separate from or in addition to those related to NGF was also suggested by the observation that the effect of these compounds was additive to NGF even at optimal NGF concentrations. No NGF agonists or partial agonists (agents known to act as NGF ligands at NGF receptors) have been described.

Several approaches have been used to deduce which domains of the NGF molecule interact with NGF receptors. Synthetic peptides with sequences corresponding to four regions of NGF have been tested for their ability to inhibit NGF neurotrophic activity. Peptides corresponding to NGF region 28–38 inhibited (i.e., they were NGF antagonists), in a sequence-specific manner, NGF neurotrophic effects on DRG neurons, but not those of CNTF or phorbol ester (Longo et al., "The in vitro biological effect of nerve growth factor is inhibited by synthetic peptides", Cell Regulation 1:189–195 (1990)). Subsequent NGF crystallography studies revealed that NGF contained three hydrophilic β-hairpin loops which were situated at NGF's surface and thus constituted likely candidates for receptor interaction sites (McDonald et al., "New protein fold revealed by a 2.3-A resolution crystal structure of nerve growth factor." Nature 354:411–414 (1991)). One of these β-hairpin loops was formed by the NGF 29–35 region. Studies from two additional laboratories have confirmed that region 29–35 peptides can inhibit NGF activity in a sequence-specific manner (Ross et al, Soc. for Neurosci. Abstr., v20(1–2) p678, Abstr. 289.2 and 289.3 (1994); LeSauteur et al, "Small peptide mimics of nerve growth factor bind TrkA receptors and affect biological responses." J. Biol. Chem., 270:6564–6569 (1995)). Recombinant molecules containing modified residues in this region or consisting of various combinations of NGF and BDNF demonstrated that NGF region 25–36 along with other β-hairpin loop and non-loop regions significantly influenced NGF/NGF-receptor interactions (Ibanez et al., "Chimeric molecules with multiple neurotrophic activities reveal structural elements determining the specificities of NGF and BDNF", EMBO J. 10:2105–2110 (1991); Suter et al., 1992; Ibanez et al., "Disruption of the low affinity receptor-binding site in NGF allows neuronal survival and differentiation by binding to the trk gene product" Cell 69:329–341 (1992); Ibanez et al., "An extended surface of binding to Trk tyrosine kinase receptors in NGF and BDNF allows the engineering of a multifunctional pan-neurotrophin", EMBO J. 12:2281–2293 (1993), Ilag et al., "Role of variable β-hairpin loop in determining biological specificities in neurotrophin family", J. Biol. Chem. 269:19941–19946 (1994)). U.S. Pat. No. 5,349,055 describes NGF mutants in the β-hairpin loop regions 25–36 and 95 which have reduced binding to $p75^{LNGFR}$ (low affinity NGF receptor). WO 90/10644 describes polypeptides corresponding to regions 90–103 and 23–35 of native NGF and their use to raise antibodies to NGF. EP 0 476 933 A1 discloses cyclic peptide analogs of HCNP (Hippocampal Cholinergic Neurotrophic Peptide), but no NGF agonist activity was described. Polyclonal antibodies raised against individual NGF β-hairpin loop peptides also indicated that multiple domains influence NGF function (Murphy et al., "Immunological relationships of NGF, BDNF, and NT-3: Recognition and functional inhibition by antibodies to NGF", J. Neurosci., 13:2853–2862 (1993)).

The complexity of NGF/NGF-receptor interactions has been further described by McDonald and Chao, "Structural determinants of neurotrophic action", J. Biol. Chem.

270:19669–19672 (1995). NGF interacts with cell surface low affinity (p75$^{LNGFR}$, referred to as p75) and high affinity (p140$^{trk}$, referred to as Trk) receptors. In one model for signal generation by NGF, p75 is required for formation of high-affinity NGF binding sites via p75-Trk heterodimers (Mahadeo et al., "High affinity nerve growth factor binding displays a faster rate of association than p140$^{trk}$ binding", *J. Biol. Chem.* 269:6884–6891 (1994)). In another model, Trk is capable of functioning independently (Clary et al., "TrkA cross-linking mimics neuronal responses to nerve growth factor", *Mol. Biol. of the Cell* 5:549–563 (1994)), although p75 can modulate NGF-induced Trk activity (Verdi et al., "p75$^{LNGFR}$ regulates Trk signal transduction and NGF-induced neuronal differentiation in MAH cells", *Neuron* 12: 733–745 (1994)). The existence of NGF dimers (Angeletti et al., "Subunit structure and amino acid composition of mouse submaxillary gland nerve growth factor", *Biochem.* 10:463–469 (1971)) is compatible with models in which NGF activates receptors by mediating formation of receptor homo- or heterodimers. Potential p75 functions which may occur independently of Trk include mediation of NGF-stimulated invasion of extracellular matrix by melanoma cells (Herrmann et al, "Mediation of NGF-stimulated extra-cellular matrix invasion by the human melanoma low-affinity p75 neurotrophin receptor: Melanoma p75 functions independently of trkA", *Mol. Biol. of the Cell* 4:1205–1216 (1993)), NGF-mediated inhibition of apoptosis, (Taglialatela et al, "Effect of p140trkA suppression on NGF and BDNF rescue of apoptotic PC12 cells", *Soc. Neurosci. Abst.* 21:1061 (1995)) and induction of sphingomyelin hydrolysis (Dobrowsky et al, "Activation of the sphingomyelin cycle through the low-affinity neurotrophin receptor", *Science*, 265:1596–1599 (1994)).

Despite this degree of ligand-receptor complexity, and despite the fact that previous peptide analogs of NGF have been NGF antagonists, it has been surprisingly discovered that a class of analogs of nerve growth factor amino acid sequences have NGF agonist activity.

2. Summary of Related Art

Small Peptide Mimics of Nerve Growth Factor Bind TrkA Receptors and Affect Biological Responses; L LeSauteur, L. Wei, B. F. Gibbs, and H. U. Saragovi; *The Journal of Biological Chemistry*, 270:6564–6569, (1995); described cyclic NGF antagonist peptides derived from the β-turn hairpin loop of NGF.

The In Vitro Biological Effect of Nerve Growth-Factor Is Inhibited by Synthetic Peptides; F. M. Longo, T. H. Vu, and W. C. Mobley; *Cell Regulation*, 1:189–195, (1990); described NGF antagonist peptides from the mouse NGF region 26–40.

Conformationally Constrained Peptides Block NGF binding; G. M. Ross et al.; *24th Ann. Mtg. Soc. Neurosci., Soc. for Neurosci. Abs.*, 20:1–2, Abstract 289.2 (1994); describes conformationally constrained peptide antagonists derived from NGF.

Peptide Mimics of an NGF Domain Inhibit Kindling and Neuronal Sprouting in Rats; K. Rashid, C. E. E. M. Van der Zee, G. M. Ross, C. A. Chapman, R. J. Racine, R. J. Riopelle, and M. Fahnestock; *24th Ann. Mtq. Soc. Neurosci.*, 20:1–2 Abstract 289.3 (1994); describes bicyclic peptide NGF antagonists.

Neurotrophic Peptide Derivatives; European Patent No. 0 476 933 A1; Y. Ueki, N. Fukushima, Y. Okeda, T. Nishihara, K. Ono, and T. Irie, (1992); discloses neurotrophic cyclic disulfide bridged peptides related to Hippocampal Cholin-ergic Neurotrophic Peptide.

SUMMARY OF THE INVENTION

This invention provides compounds displaying NGF agonist or partial agonist activity, wherein the compounds comprise a sequence of amino acid residues or biologically functional equivalents thereof, the sequence being substantially homologous to residues 29–38 of NGF, residues 43–47 of NGF or residues 92–97 of NGF, the sequence further comprising a penicillamine residue or a cysteine residue.

This invention provides compounds displaying NGF agonist activity, wherein the compounds comprise a multimer of a sequence of amino acid residues or biologically functional equivalents thereof, the sequence being substantially homologous to residues 29–38 of NGF, residues 43–47 of NGF or residues 92–97 of NGF. Preferably, the multimer is a cyclic dimer wherein the monomeric amino acid sequences are linked to each other by disulfide bridges. The compounds of this invention promote neurite outgrowth and support neuronal survival.

This invention also provides methods and compositions for the treatment of disorders involving NGF-responsive cells, by administering an effective amount of the multimeric NGF agonists of this invention to an individual suffering from such disorder.

BRIEF DESCRIPTION OF THE DRAWINGS

FIG. 3. screening of NGF loop 29–36 region cyclized peptides by automated MTT neurotrophic assay. Survival-promoting activity is listed as a percentage of the maximum NGF activity.

DETAILED DESCRIPTION OF THE PREFERRED EMBODIMENT

Figure 1:
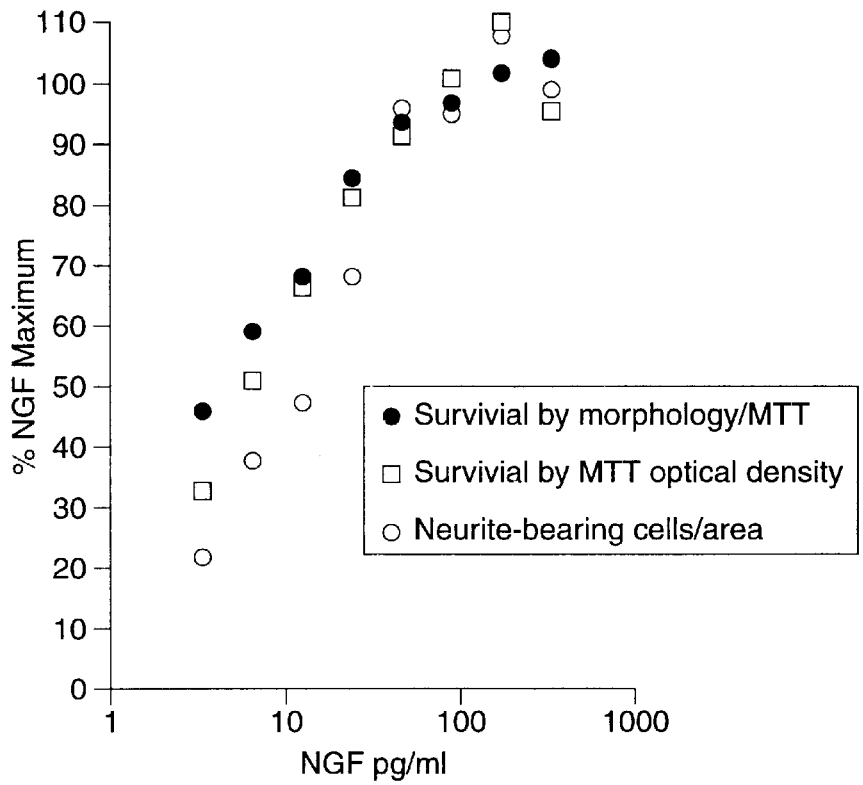
FIG. 1. Comparisons of bioassays for NGF neurotrophic activity. Chick embryo DRG neurons were cultured as described in methods. MTT was added to wells 16 hours after seeding. NGF neurotrophic effect was assessed by three methods. Morphology/MTT: (filled circles): cells were fixed 24 hours after seeding and the number of surviving cells per well was determined using phase contrast microscopy. Large, round cells without fragmented cell surfaces or accumulations of vesicles and containing blue MTT product were counted as surviving. MTT optical density (squares): at 24 hours cells were lysed, blue MTT product dissolved into solution and the optical density of each well measured by spectrophotometry as described in methods. Neurite-bearing cells/area (open circles): cells were fixed at 24 hours and cells having a process at least 2 cell diameters in length were counted under phase contrast microscopy. Data for all three methods were obtained from the same bioassay (average of duplicate wells for each NGF concentration).

The following definitions are set forth to illustrate and define the meaning and scope of the various terms used to describe the invention herein.

The term "alkyl" refers to a branched or straight chain acyclic, monovalent saturated hydrocarbon radical of one to twenty carbon atoms.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "cycloalkyl" refers to a monovalent saturated carbocyclic radical of three to twelve carbon atoms, which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "cycloalkyl lower-alkyl" refers to a cycloalkyl group appended to a lower-alkyl radical. This term is exemplified by, but not limited to, groups such as cyclopropylmethyl, cyclopentylmethyl, cyclopentylethyl, and cyclopentylpropyl.

The term "alkylene" refers to a divalent straight chain or branched chain saturated aliphatic radical.

The term "aryl" refers to an aromatic monovalent carbocyclic radical having a single ring (e.g., phenyl) or two condensed rings (e.g., naphthyl), which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Alternatively, two adjacent positions of the aromatic ring may be substituted with a methylenedioxy or ethylenedioxy group.

The term "aralkyl" refers to an aryl group appended to a lower-alkyl radical. This term is exemplified by, but not limited to, groups such as benzyl, 2-phenylethyl and 2-(2-naphthylethyl).

The term "lower-alkoxy" refers to the group —O—R where R is lower-alkyl.

The term "lower-alkoxycarbonyl" refers to the group —C(O)OR where R is lower-alkyl.

The term "acyl" refers to the group —C(O)—R, where R is alkyl, e.g., methylcarbonyl (acetyl) and ethylcarbonyl (propionyl or propanoyl).

The term "carbamoyl" refers to the group —C(O)NR'R where R and R' are independently hydrogen or lower-alkyl, e.g., where R is hydrogen and R' is lower-alkyl the group is mono-lower-alkylcarbamoyl, where R and R' are lower-alkyl the group is di-lower-alkylcarbamoyl.

The term "halo" refers to fluoro, bromo, chloro and iodo.

The term "lower-alkylthio" refers to the group R—S—, where R is lower-alkyl.

The term "lower-alkylsulfinyl" refers to the group R—S(O)—, where R is lower-alkyl.

The term "lower-alkylsulfonyl" refers to the group R—S(O)$_2$—, where R is lower-alkyl.

The term "lower-alkoxysulfonyl" refers to the group RO—S(O)$_2$—, where R is lower-alkyl.

The term "hydroxysulfonyl" refers to the group HO—S(O$_2$)—.

The term "aryloxy" refers to the group R—O— where R is an aryl group, such as for example phenoxy.

The term "arylamino" refers to the group R—NH— where R is an aryl group, such as for example, phenylamino.

The term "diarylamino" refers to the group R(R')—N— where R and R' are aryl groups such as for example, diphenylamino.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine, and the like.

An "NGF agonist" or "N6F partial agonist" is defined as any compound capable of promoting at least one of the biological responses normally associated with NGF. For example, any compound capable of supporting any one of neuronal attachment, neuronal survival, or neurite outgrowth, in the absence of NGF is defined as an NGF agonist.

The term "substantially homologous" means that the amino acid sequence of a particular compound bears a substantial correspondence to the amino acid sequence of native murine or human NGF or other members of the neurotrophin family. Typically, the residues of an amino acid sequence of the particular compound will be at least about 50%, preferably at least about 75%, more preferably at least about 90% homologous to the residues of the amino acid sequence of native NGF. Alternatively, at least about 50%, preferably at least about 75%, more preferably at least about 90% of the amino acid sequence will be composed of residues which are biologically functional equivalents of the corresponding residues in NGF.

Biologically functional equivalents of amino acids include those amino acids of similar polarity or structure to the parent amino acid such that the thus derived sequence still possesses NGF agonist activity. Exemplary members of the neurotrophin family are N6F, BDNF, NT-3 and NT-4/5. They all interact with the P75 NGF receptor. Thus the peptides of this invention are mimicking all of these neurotrophin family members.

Biologically functionally equivalent substitutes for a parent amino acid may be selected by choosing another amino acid or amino acid analog which is in the same class as the parent amino acid. For example, the nonpolar (hydrophobic) amino acids include alanine, leucine, isoleucine, norleucine, valine, norvaline, proline, phenylalanine, tyrosine, tryptophan, cysteine and methionine, methionine oxide and methionine dioxide. Amino acids with aromatic side chains include phenylalanine, tyrosine and tryptophan. The polar neutral amino acids include glycine, serine, homoserine (Hse), threonine, cysteine, tyrosine, asparagine and glutamine. The positively charged amino acids include arginine, homoarginine, ornithine, histidine and lysine. The negatively charged amino acids include aspartic acid and glutamic acid.

Biologically functional equivalents of amino acids also include the peptoid or peptidomimetic compounds such as the sulfonic and boronic acid analogs of amino acids. Other peptidomimetics which are biologically functional equivalents of amino acid sequences are also useful in the compounds of the present invention and include compounds having one or more amide linkages optionally replaced by an isostere. In the context of the present invention, for example, —CONH— may be replaced by —CH$_2$NH—, —NHCO—, —SO$_2$NH—, —CH$_2$O—, —CH$_2$CH$_2$—, —CH$_2$S—, —CH$_2$SO—, —CH=CH— (cis or trans), —COCH$_2$—, —CH(OH)CH$_2$— and 1,5-disubstituted tetrazole such that the radicals linked by these isosteres would be held in similar orientations to radicals linked by —CONH—. For a general review of these and other isosteres see, Spatola, A. F., in *Chemistry and Biochemistry of Amino Acids, Peptides and Proteins,* B. Weinstein, eds., Marcel Dekker, New York, p. 267 (1983). See also, Spatola, A. F., *Peptide Backbone Modifications* (general review), Vega Data, Vol. 1, Issue 3, (March 1983); Morley, *Trends Pharm Sci* (general review), pp. 463–468 (1980); Hudson, D. et al., *Int J Pept Prot Res,* 14:177–185 (1979) (—CH$_2$NH—, CH$_2$CH$_2$—); Spatola et al., *Life Sci,* 38:1243–1249 (1986) (—CH$_2$—S); Hann *J. Chem. Soc. Perkin Trans.* I, 307–314 (1982) (—CH—CH—, cis and trans); Almquist et al., *J Med Chem,* 23:1392–1398 (1980)

(—COCH₂—); Jennings-White et al., *Tetrahedron Lett*, 23:2533 (1982) (—COCH₂—); Szelke et al., European Appln. EP 45665 CA: 97:39405 (1982) (—CH(OH)CH₂—); Holladay et al., *Tetrahedron Lett*, 24:4401–4404 (1983) (—C(OH)CH₂—); and Hruby, *Life Sci*, 31:189–199 (1982) (—CH₂—S—); each of which is incorporated herein by reference. The C-terminal carboxylic acid can be replaced by a boronic acid —B(OH)₂ or boronic ester —B(OR)₂ or other such boronic acid derivative as disclosed in U.S. Pat. No. 5,288,707, incorporated herein by reference. Compounds and fragments having isosteric replacements may have significant advantages over those compounds and fragments with the natural amide linkages. Some of the advantages include, for example: more economical production, greater chemical stability, enhanced pharmacological properties (half-life, absorption, potency, efficacy, etc.), altered specificity (e.g., a broad-spectrum of biological activities), reduced antigenicity, and others. The compounds of the present invention may also be labeled via covalent attachment of one or more labels, directly or through a spacer (e.g., an amide group), to position(s) on the compound that are predicted by quantitative structure-activity data and/or molecular modeling to be non-interfering. Additionally, derivatization (e.g., labeling) of compounds should not substantially interfere with the desired biological or pharmacological activity of the compound.

In the context of the present invention, biologically functional equivalents of amino acid sequences also include sequences in which one or more nucleophilic side chains (OH, NH₂, SH and COOH) are blocked by a protecting group as described herein, such that the resulting compound still retains NGF agonist activity.

For the compounds of the invention which contain amino acid or peptide fragments, the amino acid residues are denoted by single-letter or three-letter designations following conventional practices. The designations for geneencoded amino acids are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Commonly encountered amino acids which are not geneencoded may also be used in the present invention. These amino acids and their abbreviations include ornithine (Orn); aminoisobutyric acid (Aib); benzothiophenylalanine (BtPhe); albizziin (Abz); t-butylglycine (Tle); phenylglycine (PhG); cyclohexylalanine (Cha); norleucine (Nle); 2-naphthylalanine (2-Nal); 1-naphthylalanine (1-Nal); 2-thienylalanine (2-Thi); 1,2,3,4-tetrahydroisoquinoline-3-carboxylic acid (Tic); N-methylisoleucine (N-MeIle); homoarginine (Har); Nα-methylarginine (N-MeArg); phosphotyrosine (pTyr or pY); pipecolinic acid (Pip); 4-chlorophenylalanine (4-ClPhe); 4-fluorophenylalanine (4-FPhe); 1-aminocyclopropanecarboxylic acid (1-NCPC); and sarcosine (Sar).

All of the amino acids used in the present invention may be either the D- or L-isomer. The L-isomers are preferred when not otherwise specified.

The term "neurodegenerative disorder" refers to a disease state in a mammal which can include degenerative growth and disorder of the nervous system which can respond to treatment with NGF or NGF-derived peptides. Thus, diseases characterized by the loss of function and or/degeneration of neurons and nerves are within the scope of this invention. In addition, any disease that can respond to NGF-responsive cells with the present invention is within the scope of the present invention. Exemplary disorders include without limitation, Alzheimer's disease, Down's syndrome, Creutzfeldt-Jacob disease, kuru, scrapie, transmissible mink encephalopathy, Huntington's disease, apoptosis, Riley-Day familial dysautonomia, multiple system atrophy, neuropathies, amyotrophic lateral sclerosis (ALS) and the like. Additionally, neural tumors such as neuroblastomas may also be responsive to the NGF agonists of this invention. other pathological states include ischemia, hypoxia and neural injury.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

As used herein, the term "therapeutically effective amount" refers to that amount of a compound of the present invention which, when administered to a mammal in need thereof, is sufficient to effect treatment (as defined above) of a neurodegenerative disorder. The amount that constitutes a "therapeutically effective amount" will vary depending on the compound, the condition or disease and its severity, and the mammal to be treated, its weight, age, etc., but may be determined routinely by one of ordinary skill in the art with regard to contemporary knowledge and to this disclosure.

The term "linking group" refers to any chemically and biologically compatible covalent grouping of atoms which can serve to link together the monomeric amino acid sequences disclosed by this invention. Generally, preferred linking groups have from 0–20 carbons, preferably 0–8 carbons, more preferably 0–3 carbons and/or 0–10 heteroatoms (NH, O, S, P etc.) and may be branched or straight chain or contain rings. The linkage can be designed to be hydrophobic or hydrophilic or adopt a particular spatial conformation to maximize the NGF agonist property of the multimeric species disclosed herein. The linking group can contain single and/or double bonds and saturated or aromatic rings. The linking group may contain groupings such as amide, ester, phosphate, ether, sulfide, disulfide, amine and the like.

The present invention provides compounds displaying NGF agonist or partial agonist activity, wherein the compound comprises a sequence of amino acid residues or biologically functional equivalents thereof, the sequence being substantially homologous to residues 29–38 of NGF, residues 43–47 of NGF or residues 92–97 of NGF, the amino acid sequence further comprising a penicillamine residue or a cysteine residue.

Another aspect of this invention relates to compounds having sequences of amino acid residues or biological functional equivalents thereof, the sequence being substantially homologous to residues 29–38 of NGF, residues 43–47 of NGF or residues 92–97 of NGF, wherein a fragment of the sequence of amino acids is in a conformationally constrained structure such as a ring and the sequence of amino acids further comprises at least one cysteine or at least one penicillamine residue. Such constrained structures can be derived by several methods including, but not limited to:

(1) Cyclizing the N-terminal amine with the C-terminal carboxylic acid either via direct amide bond formation between the nitrogen and the C-terminal carbonyl, or via the intermediacy of spacer group such as for example by condensation with an ε-amino carboxylic acid, (2) Cyclizing via the formation of a bond between the side chains of two residues, e.g., by forming a amide bond between an aspartate or glutamate side chain and a lysine side chain, or by disulfide bond formation between two cysteine side chains or between a penicillamine and cysteine side chain or between two penicillamine side chains, (3) Cyclizing via formation of an amide bond between a side chain (e.g., aspartate or lysine) and either the N-terminal amine or the C-terminal carboxyl respectively, (4) Linking two side chains via the intermediacy of a short carbon spacer group.

Preferably, the sequence of amino acid residues or their biological functional equivalents will be derived from residues 29–38 of NGF and the cyclic structure will be such that the resulting compound will simulate the β-hairpin loop of residues 28–40 of NGF. Representative cyclic peptides are:

| L29 | CTDIKGKEPen—NH$_2$ | SEQ ID NO:1 |
| L43 | PenNINNSC—NH$_2$ | SEQ ID NO:2 |
| L92 | PenTDEKQAC—NH$_2$ | SEQ ID NO:3 | where Pen represents penicillamine.

Another aspect of this invention relates to compounds comprising multimers (i.e., dimers, trimers and the like) of a sequence of amino acid residues or biologically functional equivalents thereof, the sequence being substantially homologous to residues 29–38 of NGF, residues 43–47 of NGF or residues 92–97 of NGF. Multimers derived from the sequence of NGF residues 29–38 are preferred. The multimer can be a homomultimer by which is meant that the multimer is composed of two identical monomers, i.e., each monomer is the same amino acid sequence. Alternatively, the multimer can be a heteromultimer, by which is meant that one monomer is a first amino acid sequence derived from one of the above regions of NGF and the other monomer is a different amino acid sequence derived from that same region of NGF.

The monomer units may be linked together to provide the multimers in a linear or branched fashion, in the form of a ring (for example, a macrocycle), in the form of a star (dendrimers) or in the form of a ball (e.g., fullerenes). Skilled artisans will readily recognize a multitude of polymers which can be formed from the monomeric sequences disclosed herein. In a preferred embodiment, the multimer is a cyclic dimer. Using the same terminology as above, the dimer can be a homodimer or a heterodimer. The cyclic dimers can be formed by linking the individual monomers to each other by any of linkages described above, such as but not limited to, for example:

(1) Cyclizing the N-terminal amines with the C-terminal carboxyl group of the other monomer either via direct amide bond formation between the nitrogen and the C-terminal carbonyl, or via the intermediacy of spacer group such as for example by condensation with an ε-amino carboxylic acid, (2) Cyclizing via the formation of bonds between the side chains of residues on the two monomers, e.g., by forming a amide bond between an aspartate or glutamate side chain on one monomer and a lysine side chain on the other monomer, or by disulfide bond formation between two cysteine side chains or between a penicillamine and cysteine side chain or between two penicillamine side chains, (3) Cyclizing via formation of an amide bond between a side chain on one monomer (e.g., aspartate or lysine) and either the N-terminal amine or the C-terminal carboxyl respectively on the other monomer, (4) Linking side chains via the intermediacy of a short carbon spacer group.

In general, multimers (especially dimers) of the sequences disclosed herein, made by any method either presently known, or that become known to one of skill in the art, are contemplated as within the scope of this invention.

Since cyclic dimer formation requires the formation of two bonds between the monomers, it will be apparent that any combination of the above methods can also be used. In a preferred embodiment, the amino acid sequence further comprises at least one cysteine or at least one penicillamine residue. In other embodiments, two residues of the amino acid sequence have sulfhydryl carrying side chains, e.g., a penicillamine and a cysteine and dimerization is via the formation of disulfide bridges between these residues.

The cyclic dimers of this invention are represented by Formulas I and II where X represents a sequence of amino acid residues or biologically functional equivalents thereof, the sequence being substantially homologous to residues 29–38 of NGF, residues 43–47 of NGF or residues 92–97 of NGF. $R_1$ is attached to the N-terminal amino group of X and is selected from the group consisting of hydrogen, lower alkyl, lower acyl, lower alkoxy carbonyl, lower alkylamino carbonyl, lower alkenyl, lower alkynyl, aryl, aroyl, lower aryloxy carbonyl and lower arylamino carbonyl; $R_2$ is attached to the C-terminal carbonyl group of X and is selected from the group consisting of OH, $NH_2$, NH(R), $NR_2$, NR'R", $OR_3$, $NH(CH_2)_nB(OH)_2$ and $NH(CH_2)_nB(OR)_2$, where R, R' and R" are lower alkyl or aryl. Formula I represents a head to head cyclic dimer and Formula II represents a head to tail cyclic dimer. $A_1$ and $A_2$ represent linking groups between the two monomers as described above. Other representative linking groups (referred to as spacers) are described in U.S. Pat. No. 5,470,932, col. 5, lines 1–20; U.S. Pat. No. 5,470,843, col. 11, line 39 through col. 12, line 33; and U.S. Pat. No. 5,470,997, col. 2, line 40 through col. 3, line 5. Preferably, the sequence X further comprises a penicillamine residue and a cysteine residue and $A_1$ and $A_2$ represent a disulfide linkage between the penicillamine and cysteine residues. Preferably, the sequence of amino acid residues between the cysteine and the penicillamine residue will comprise at least 5 residues of the sequence KGKEV (residues 3 to 7 of SEQ ID NO:4) or biological equivalents thereof.

CYCLIC DIMERS

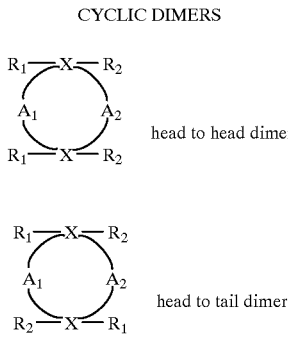

Formula I — head to head dimer

Formula II — head to tail dimer

The multimers can be formed by the direct attachment of the monomers to each other. Alternatively, linking groups $A_1$ and $A_2$ can be added to the monomeric sequences to join the monomers together. Often, this will involve using bifunctional spacer units (either homobifunctional or heterobifunctional) as are known to one of skill in the art. By way of example and not limitation, many methods for incorporating such spacer units in linking peptides together using reagents such as succinimidyl-4-(p-maleimidomethyl) cyclohexane-1-carboxylate (SMCC), succinimidyl-4-(p-maleimidophenyl)butyrate and the like are described in the Pierce Immunotechnology Handbook (Pierce Chemical Co., Rockville, Ill.) and are also available from Sigma Chemical Co. (St. Louis, Mo.) and Aldrich Chemical Co. (Milwaukee, Wis.) and described in "Comprehensive Organic Transformations", VCK-Verlagsgesellschaft, Weinheim/Germany (1989). One example of a linking group which may be used to link the monomeric sequences together is —$Y_1$—F—$Y_2$— where $Y_1$ and $Y_2$ are identical or different and are alkylene groups of 0–20, preferably 0–8, more preferably 0–3 carbon atoms, and F is one or more functional groups such as —O—, —S—, —S—S—, —C(O)—O—, —NR—, —C(O)—NR—, —NR—C(O)—O—, —NR—C(O)—NR—, —NR—C(S)—NR—, —NR—C(S)—O—. $Y_1$ and $Y_2$ may be optionally substituted with hydroxy, alkoxy, hydroxyalkyl, alkoxyalkyl, amino, carboxyl, carboxyalkyl and the like. It will be understood that any appropriate atom of the monomer can be attached to the linking group.

Specific cyclic dimers corresponding to the NGF sequence of residues 29–38 linked by disulfide bridges are depicted below. The cyclic dimers are shown in the C-terminal carboxamide form. It will be understood that the corresponding C-terminal carboxylic acids are also within the scope of this invention.

Cyclic dimers for P7

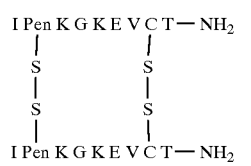

Cyclic dimers for P8

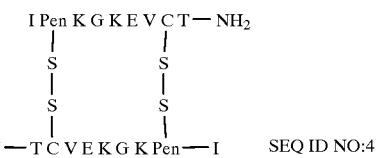

SEQ ID NO:4

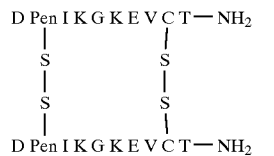

SEQ ID NO:5

Cyclic dimers for P9

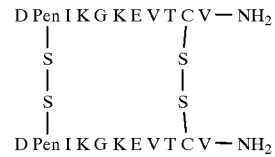

SEQ ID NO:6

Cyclic dimers for P10

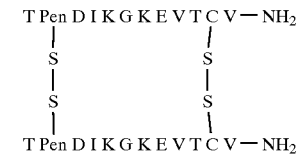

SEQ ID NO:7

Cyclic dimers for P11

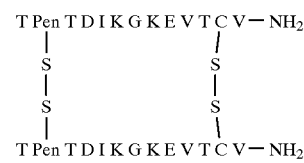

-continued

Cyclic dimers for 7P (continued)

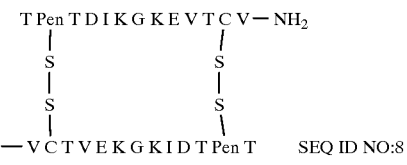

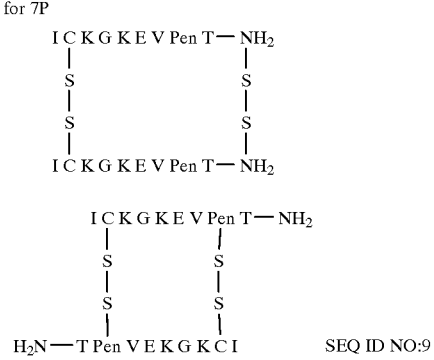
SEQ ID NO:8

Cyclic dimers for 7P

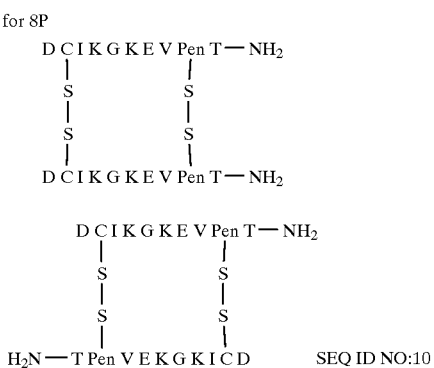
SEQ ID NO:9

Cyclic dimers for 8P

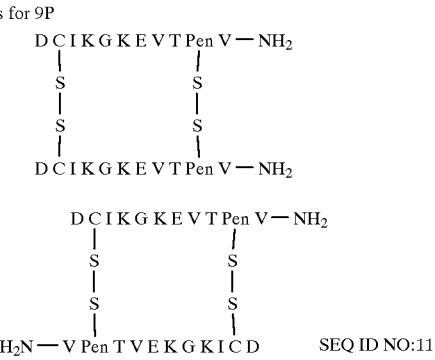
SEQ ID NO:10

Cyclic Dimers for 9P

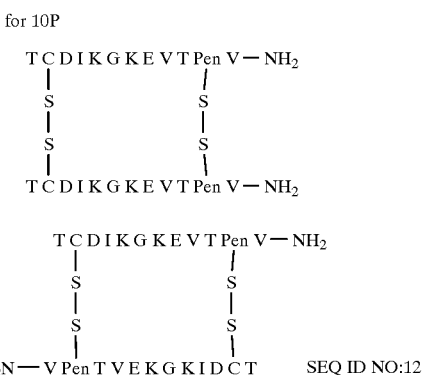
SEQ ID NO:11

Cyclic dimers for 10P

SEQ ID NO:12

Cyclic dimers for 11P

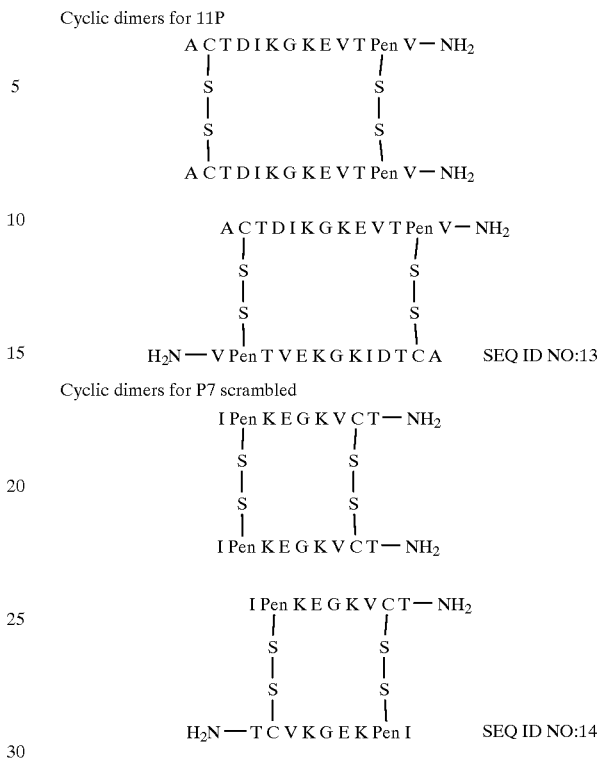
SEQ ID NO:13

Cyclic dimers for P7 scrambled

SEQ ID NO:14

The N-terminal substituent ($R_1$) of these cyclic peptides includes hydrogen, lower alkyl, lower acyl, lower alkenyl, lower alkynyl, aryl, aroyl, aryloxycarbonyl, aralkyloxycarbonyl, and lower alkyloxycarbonyl.

The carboxy terminal substituent ($R_2$) of these cyclic peptides includes —OH, $NH_2$, $OR_3$ where $R_3$ is lower alkyl or aryl, $NH_3$ where $R_3$ is lower alkyl or aryl and $PO_3H_2$, $B(OH)_2$, $CH_2OH$, $SO_3H$ and 5-tetrazole which replaces the COOH of the carboxyl-terminal amino acid.

It is also to be understood that the side chains, the N-terminus and the C-terminus of the amino acid sequences disclosed herein may be modified by alkylation, acylation, sulfonylation and the like. The modifiable nucleophilic groups are —OH (e.g., serine, threonine, tyrosine and the like) to give a group —OR; —$NH_2$ (e.g., lysine, ornithine and the like) to give a group —NHR or $NR_2$, —SH (e.g., cysteine, penicillamine and the like) to give a protected group —SR and COOH (e.g., glutamate, aspartate and the like) to give a group —COOR. R can be alkyl, cycloalkyl, cycloalkyl lower alkyl, acyl, aryl, arylalkyl or mono-alkylsulfonyl or di-alkylsulfonyl.

The amino acid sequences of the present invention can be synthesized in a manner similar to methods conventionally used in ordinary peptide chemistry. Such known methods are described in, for example, M. Bodansky and M. A. Ondetti, Peptide Synthesis, published by Interscience Publishing Co., New York, 1966; F. M. Finn and K. Hofmann, The Proteins, volume 2, edited by H. Neurath, R. L. Hill, Academic Press Inc., New York, 1976; Nobuo Izumiya et al., Peptide Synthesis, published by Maruzen Co., 1976; Nobuo Izumiya et al., Fundamental Peptide Synthesis and Experiment, published by Maruzen Co., 1985; Lecture Series on Biochemical Experiment, edited by the Association of Biochemistry, Japan, volume 1, "Chemistry of Protein IV", chapter II, Haruaki Yajima, Peptide Synthesis, 1977. That is the peptide can be synthesized by selecting the liquid phase method or the solid phase method, depending on the structure of the peptide.

In more detail, where peptides contain a partial structure of —COOH or —CONH$_2$ at the C-terminus, the peptides can be obtained by any of the liquid phase method and the solid phase method but in other cases, the liquid phase method is rather preferred.

For example, in the case that the peptide derivative is synthesized by the solid phase method, the C-terminal amino acid (amino group-protected amino acid) or the C-terminal substituent (the substituent having carboxyl group; in the case that an amino group is contained, the amino group is protected) is bound to an insoluble carrier through the carboxyl group. If necessary and desired, after the amino protective group is removed, the amino group-protected amino acids or the amino acid derivatives (in the case that a free amino group is present, the amino group is protected) are successively coupled, according to the amino acid sequence of the desired peptide, through condensation of the reactive carboxyl groups with the reactive amino groups or with the reactive hydroxy groups. The synthesis is carried out step by step. If necessary, after the selected side chain protective group is removed, cyclization reaction may be carried out. After synthesis of the whole sequence, the N-terminal substituent is condensed, if necessary. Then, the peptide is withdrawn from the insoluble carrier and at the same time, the protective groups are removed. Further if necessary and desired, the N-terminal substituent or C-terminal substituent is condensed and the protective group is removed to obtain the desired amino acid sequence. Further, if necessary, the desired bond is finally formed between the side chains to obtain the cyclic peptide. In the case of disulfide bond formation between cysteine and penicillamine residues, this is accomplished by oxidation.

In the case of synthesis by the liquid phase method, the C-terminal amino acid having a free amino group at the terminal (carboxyl group-protected amino acid) or the C-terminal substituent (the substituent having free amino or hydroxy group; in the case that a carboxyl group is present, the carboxyl group is protected) is successively coupled with the amino group-protected amino acid or the amino acid derivatives (in the case that a free amino group is present, the amino group is protected), according to the amino acid sequence of the desired peptide, through condensation of the reactive amino groups or the reactive hydroxy groups with the reactive carboxyl groups. If necessary, the N-terminal substituent is finally condensed therewith. Further if necessary, the N-terminal amino acid may be derivatized. Thus, the whole sequence can be synthesized. The whole sequence may also be synthesized by synthesizing fragments of the sequence in a similar manner, removing the selected protective groups and coupling the resulting peptide fragments to each other. The protective group is removed and if necessary, the N-terminal substituent or the C-terminal substituent is condensed and the protective group is removed to obtain the desired peptide. Moreover, the desired cyclic bond is finally formed between the side chains and, if necessary, the protective group is removed to obtain the cyclic amino acid sequence.

In the methods described above, the reactive functional groups are preferably protected.

Examples of the protective group of the amino group include benzyloxycarbonyl, t-butyloxycarbonyl, p-methoxybenzyloxycarbonyl, 2-chlorobenzyloxycarbonyl, p-toluenesulfonyl, trifluomacetyl, phthalyl, formyl, o-nitrophenylsulfenyl, 3-nitro-2-pyridinesulfenyl, diphenylphosphinothioyl, etc. Examples of the protective group of the carboxyl group include alkyl esters (esters of C1–C4 such as methyl, ethyl, t-butyl, etc.), benzyl ester, p-nitrobenzyl ester, p-methylbenzyl ester, cyclohexyl ester, cyclopentyl ester, etc. Examples of the protective group of the mercapto group include benzyl, p-methoxybenzyl, 4-methylbenzyl, trityl, benzhydryl, acetamidomethyl, 3-nitro-2-pyridinesulfenyl, t-butyl, etc. The hydroxy group in Ser, Tyr, etc., may not be necessarily protected but if necessary, can be protected with benzyl, 2,6-dichlorobenzyl, t-butyl, benzyloxycarbonyl, acetyl, etc. The indolyl group in Trp, etc., may be protected, if necessary, with formyl, benzyloxycarbonyl, 2,4-dichlorobenzyloxycarbonyl, etc. The guanidino group may also be protected in the state protonated with hydrochloric acid, etc. But, if necessary, it may also be protected with p-toluene-sulfonyl, nitro, benzyloxycarbonyl, p-methoxybenzenesulfonyl, mesitylene-2-sulfonyl, etc. In the methods described above, peptide bonds can be formed by known methods, for example, the method using condensing agents of carbodiimide type such as dicyclohexyl-carbodiimide, 1-ethyl-3-(3-dimethylaminopropyl)carbodiimide, etc.; the symmetrical acid anhydride method, the mixed acid anhydride method, the azide method, the activated ester method, the oxidation-reduction method, the diphenylphosphoryl azide method, the method using carbodiimide type condensing agent and additives (1-hydroxybenzotriazole, N-hydroxysuccinimide, etc.).

For removing the protective group, there are known, for example, the trifluoroacetic acid method, the methane-sulfonic acid method, the trifluoromethanesulfonic acid method, the hydrogen fluoride method, the liquid ammonia-sodium method, the catalytic reduction method, the alkali saponification method, etc.

The peptides produced by the present invention can be purified by using known methods conventionally used in the art of peptide chemistry, singly or in combination, such as ion exchange chromatography, partition chromatography, gel chromatography, reverse phase liquid chromatography, etc.

Compounds of this invention possesssing NGF agonist activity can be identified by using the neurotrophic activity screening assays described in more detail in the examples. Briefly, target compounds are incubated with sensory neurons and cell morphology is assessed to determine neuronal survival and neurite outgrowth. Alternatively, the MTT assay (as described in more detail in the Examples) is performed to detect the presence of viable neurons. Viable neurons selectively take up MTT (3-(4,5-diethylthiazol-2-yl)-2,5-diphenyl tetrazolium bromide) and produce an insoluble blue formazan product in the cell body. Appropriate control experiments are done either in the presence of NGF (positive controls) or in the absence of target (negative controls) to determine both whether the target compounds have NGF activity relative to the controls and the magnitude of this activity.

The NGF agonist compounds of this invention can be used to treat any disease or neurodegenerative disorder in which NGF itself is useful. In addition, since the preferred compounds of this invention are much smaller in size than NGF, they are therefore more amenable to passing the blood-brain barrier when desired and are less likely to elicit an adverse immunological response. The compounds of this invention can be used to promote the growth and/or survival of cells of the nervous system, including, but not limited to, dopaminergic neurons, cholinergic neurons, sensory neurons, striatal cells, cells of the cortex, striatum, hippocampus, cerebellum, olfactory bulbs, peraqueductal gray, raphe nuclei, locus coeruleus, dorsal root ganglion, neural placode derivatives, sympathetic neurons and lower motor neurons.

The NGF agonist compounds described herein may be particularly useful for the treatment of diseases or disorders which involve damage to both sensory and motor neurons, including for example, damage caused by chemotherapy or neuropathies such as those associated with diabetes. In the central nervous system, the NGF agonists of this invention may provide improved diffusion characteristics over native NGF, thus providing useful means of treating diseases such as Alzheimer's which involves loss of multiple types of neuronal cells. NGF itself causes overgrowth of neurites which in some uses would be a deleterious side-effect. One advantage of the partial agonists disclosed herein is that some forms preferentially promote survial rather than neurite outgrowth.

In a specific embodiment of this invention, the NGF agonists may be used to treat neurodegenerative disorders caused by a lack of NGF, such as for example, Huntington's disease. In this disease, cholinergic neurons in the caudate putamen degenerate. As NGF has been shown to support the differentiation of cholinergic neurons, agonist compounds may be administered to enhance the activity of the cholinergic neurons present in the caudate-putamen.

The NGF agonists of the invention may be administered by parenteral means, including subcutaneous and intramuscular injection, injection into the CNS, implantation of sustained release depots, intravenous injection, intranasal administration, and the like. Because the present compounds have the advantage of being metabolically stable and crossing the blood-brain barrier, they have the potential of being administered orally or by intravenous injection. If necessary, the compounds can be protected against proteolytic degradation by encapsulation in liposomes, gels, microcapsules, slow release formulations and the like to ensure that they are not degraded in the gut.

The NGF agonists of the present invention can be administered as a pharmaceutical composition comprising the compound in combination with a pharmaceutically acceptable excipient. Such excipients include water, saline, Ringer's solution, dextrose solution, and solutions of ethanol, glucose, sucrose, dextran, mannose, mannitol, sorbitol, polyethylene glycol, phosphate, acetate, gelatin, collagen, and the like. One may additionally include other suitable preservatives, stabilizers and antimicrobials, antioxidants, buffering agents and the like. A thorough discussion of pharmaceutically acceptable excipients is available in *Remington's Pharmaceutical Sciences,* 2nd Ed., Mack Publishing Co.

Alternatively, one may incorporate or encapsulate the NGF agonists in a suitable polymer matrix, liposome or membrane, thus providing a sustained release delivery device suitable for implantation near the site to be treated locally. In general, with sustained release delivery, the formulations are constructed so as to achieve a constant concentration which will be bioequivalent to about 100 times the serum level of NGF of 10 times the tissue concentration.

The amount of NGF agonist required to treat any particular neural disorder will of course vary depending on the nature and severity of the disorder, the age and condition of the patient, and other factors readily determined by one of skill in the art. Suitable dosages are from 10 µg/kg to about 1000 mg/kg, more preferably 10 mg/kg to about 400 mg/kg.

The NGF agonists of this invention are also useful in screening test compounds for their ability to act as agonists or antagonists of NGF. Briefly, NGF agonists of this invention are incubated with neuronal cells in the presence or absence of the test compound and cell survival, neurite outgrowth and MTT uptake is determined as described in the Examples.

Because the NGF agonists disclosed herein interact with the p75 receptor, they may also be used as affinity probes or ligands. In particular, they may be used to identify or capture p75 proteins from a mixture of different proteins. Typically, use of the polypeptides of the present invention in identifying p75 proteins in a mixture of proteins may be carried out using a Western blotting format. In particular, the mixture of proteins may be immobilized on a solid support, as described above. Immobilization may include simple spotting, electroblotting of SDS-PAGE gels and the like. The blot is then blocked using a nonspecific protein, i.e., BSA. Labeled polypeptides of the present invention may then be used to interrogate the blot, binding to the immobilized p75.

The polypeptides of the present invention may also be used as affinity ligands to purify p75 proteins from a mixture of proteins. In particular, the polypeptide of the invention is coupled to a solid support. The support bound polypeptide is then contacted with the mixture of proteins containing the p75 protein under conditions that are conducive to p75 binding. The support is then washed to remove unbound and nonspecifically bound proteins. Substantially pure p75 may then be readily eluted from the support by, e.g. a change in salt, pH or buffer concentrations.

EXAMPLES

Material and Methods

Peptide synthesis, purification and characterization

Peptides were synthesized in the C-terminal amide form on an Applied Biosystems 430A peptide synthesizer by solid-phase methods (Merrifield, 1986) using t-Boc (tertiary-butyloxycarbonyl) chemistry. In each peptide sequence, one cysteine and one penicillamine (dimethyl cysteine) residue were added to the ends of the linear sequence to provide sulfhydryl groups for peptide cyclization via oxidation. In the set of peptides listed in FIG. 3, amino acid residues were added at either end in order to flank cysteine and penicillamine moieties in an effort to further restrain peptide conformation. Boc amino acids were purchased from Bachem (Torrance, Calif.) containing the following side-chain protecting groups: asp-OBzl (benzyl ester), penicillamine-Mbzl (methyl benzyl), lys-2 chloro Z (2-chlorobenzyl), glu-OBzl, thr-Bzl (benzyl) and cys-MBzl.

Peptides were cleaved from the benzhydrylamine resin with hydrogen fluoride, washed with cold ethyl ether, precipitated in trifluoroacetate with ice-cold ethyl ether, redissolved in water and lyophilized. Peptides were stored in air-tight containers at −70° C. A fraction of each peptide preparation was resuspended at a low concentration in 4 liters of water and cyclized via oxidative formation of disulfide bonds by the dropwise addition of K3[Fe(CN)6] as previously described (Pierschbacher and Ruoslahti, "Influence of stereochemistry of the sequence Arg-Gly-Asp-Xaa on binding specificity in cell adhesion", *J. Biol. Chem.* 262:17294–17298 (1987)). Low peptide concentrations are typically used to favored formation of intramolecular disulfide bonds (cyclization) over intermolecular bonds (multimerization) although multimers are often present as a minor species. Persistence of yellow color for 5 minutes confirmed that cyclization/oxidation was complete. Cyclized/oxidized peptides were lyophilized and stored at −70° C.

Cyclized/oxidized and linear peptides were purified by reversed-phase HPLC as previously described (Longo et al., "The in vitro biological effect of nerve growth factor is inhibited by synthetic peptides", *Cell Regulation* 1:189–195 (1990)). Peptides were eluted from a semi-preparative C18 Vydac column (9×200 mm) at a flow rate of 3 ml/min. The column was equilibrated in 0.1% TFA (trifluoroacetic acid)

for 5 minutes followed by a linear gradient of acetonitrile (0 to 80%) in 0.1% TFA over 1 hr. Eluent was monitored at 230 nm and individual large peaks or groups of small peaks were collected into sterile polypropylene tubes on ice. HPLC fractions were lyophilized, resuspended in sterile water, aliquoted into sterile Eppendorf tubes and stored at −70° C. An aliquot from each fraction was used for quantitative amino acid analysis to confirm peptide composition and to determine concentration. Prior to each bioassay, peptide aliquots were lyophilized and resuspended in culture media. In some cases, remaining aliquots of HPLC fractions demonstrating neurotrophic activity were reloaded onto the above column using the same eluting conditions and subfractions were collected for further assays. Subfractions also underwent quantitative amino acid analysis. The molecular mass of peptides in selected fractions and subfractions was analyzed by matrix-assisted laser desorption/ionization (MALDI) mass spectrometry performed by AnaSpec Inc., San Jose, Calif.

Bioassays for neurotrophic activity

Bioassays were performed as previously described (Manthorpe et al, "An automated colorimetric microassay for neuronotrophic factors", *Dev. Brain Res.* 25:191–198 (1986)). Dorsal root ganglia were dissected from embryonic day 8 chick embryos and placed in calcium and magnesium-free Dulbecco's balanced salt solution on ice. Ganglia were pelleted and then resuspended and incubated for 10 min in 2.5 ml 0.01% trypsin at 37° C., washed once with 4 ml of culture medium (Dulbecco's Modified Eagle's Medium H-21 with glutamine, 1 mm pyruvate, 3.0 g/L glucose, 3.7 g/L $HCO_3$ and 10% fetal calf serum) and dissociated in 1.5 ml culture medium by gentle trituration (10–15 times) through a 1 mm diameter flamed glass pipette. The resulting cell suspension was diluted to 7 ml in culture medium, added to a 100 mm diameter plastic tissue culture dish (Falcon) and incubated for 2.5 hrs at 37° C. in 5% $CO_2$–95% air. During this incubation non-neuronal cells (Schwann cells, fibroblasts) more readily attached to the substratum leaving a supernatant containing an enriched neuronal population (80–85% neurons). Tissue culture wells (Costar A/2, 0.16 $cm^2$/well) were precoated with 50 ml/well of polyornithine (Sigma; 0.1 mg/ml in phosphate buffered saline, PBS) for 1 hr followed by 50 ml/well laminin (Gibco, 10 mg/ml in PBS) for 3 hrs. Laminin provided a substrate permissive for neurite outgrowth. Laminin-PBS was aspirated and each well received 25 ml of peptide serially diluted in culture medium and 25 ml of cell suspension (60,000 cells/ml, ~1500 neurons/well). Control cultures performed with each assay included serial dilutions of NGF to generate NGF dose-response curves and cultures without NGF or peptides to determine background survival. Background survival was typically 10–15% of that seen with optimal concentrations of NGF. Mouse submaxillary β-NGF was purified via 7S NGF as previously described (Longo et al., "The in vitro biological effect of nerve growth factor is inhibited by synthetic peptides", *Cell Regulation* 1:189–195 (1990)).

The bioassays used for measuring the NGF agonist activity of the compounds of this invention were initially characterized using NGF as a control. Preliminary assays demonstrated that NGF promoted neuronal survival as measured by the automated MTT assay. Traditional morphological assessment of peptide-supported neurons at 24 hours revealed intact cells characteristic of NGF-supported neurons; however, in most cases neurites were absent. The neurotrophic activity of NGF is most easily assessed by measuring the number of cells surviving and bearing neurites; however, the lack of neurites in peptide-supported cultures required the use of additional criteria to assess peptide effect. In order to more accurately determine neuronal survival, MTT was added to cultures at 16 hours and cultures assessed under phase contrast microscopy at 24 hours. Intact cells characteristic of surviving neurons which also contained blue MTT product were counted. Using NGF dose-response curves, three methods of measuring neurotrophic activity were compared: (1) automated MTT calorimetric assay, (2) counting the number of surviving cells bearing neurites and (3) counting the number of intact cells with blue MTT product independent of the presence or absence of neurites. As shown in FIG. 1, all three methods produced similar NGF dose-response curves. In subsequent studies, activity of both peptides and NGF was assessed by counting the number of intact cells with blue MTT product (morphological/MTT assay) and by the automated MTT assay.

The ability of cyclized/oxidized peptides to directly interact with MTT to artifactually produce MTT signal was also assessed. The presence of an already-oxidized compound would not be expected to reduce MTT and generate signal. In the absence of cells, addition of MTT to wells containing cyclized peptide dissolved in culture media generated no increment in optical density and therefore demonstrated that MTT signal would not be an artifact of cyclized/oxidized peptides.

Neuronal survival and neurite outgrowth were assessed by a combination of morphological criteria described previously (Longo et al, "The in vitro biological effect of nerve growth factor is inhibited by synthetic peptides" *Cell Regulation* 1:189–195 (1990)) and an MTT calorimetric assay (Manthorpe et al., "An automated colorimetric microassay for neuronotrophic factors", *Dev. Brain Res.* 25:191–198 (1986)). MTT is a yellow tetrazolium derivative (3-(4,5-diethylthiazol-2yl)-2,5-diphenyl tetrazolium bromide) which is taken up selectively by viable neurons and converted by reduction in the mitochondria (associated with electron transport) to a blue formazan product which fills the cell body of surviving neurons. The blue product can be quantitated by lysing cells with acid alcohol to solubilize the blue product and measuring overall optical density or by counting the number per area of intact surviving neurons with blue dye. MTT was added to cultures 16 hrs following cell seeding. In some assays, cells were fixed at 24 hours with glutaraldehyde (2% in PBS) and examined under phase contrast microscopy. Horizontal and vertical strips of each well (corresponding to approximately 30% of the total well area,) were examined and the number of surviving cells (defined as large intact cells without fragmented cell membranes or accumulations of vesicles and containing blue MTT product) as well as cells bearing a process greater than one cell diameter were counted. For each peptide or NGF concentration, duplicate wells were counted in each bioassay and four values (two strips counted/well) averaged. In other assays, cells were lysed at 24 hours in acid alcohol and the MTT product was dissolved and quantified. Optical densities from duplicate wells were averaged.

Example 1

Bioassays of L29, L43 and L92

Cyclized/oxidized peptides (L29, L43 and L92) corresponding to the three hydrophilic β-hairpin loop regions of NGF were assayed for survival-promoting activity as determined by morphologic criteria (large, round cells without fragmented cell surfaces or accumulations of vesicles and containing blue MTT product were counted as surviving).

The peptide structures were:

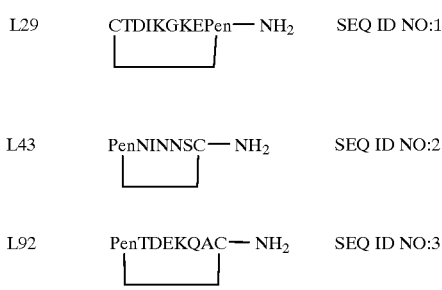

Figure 2:
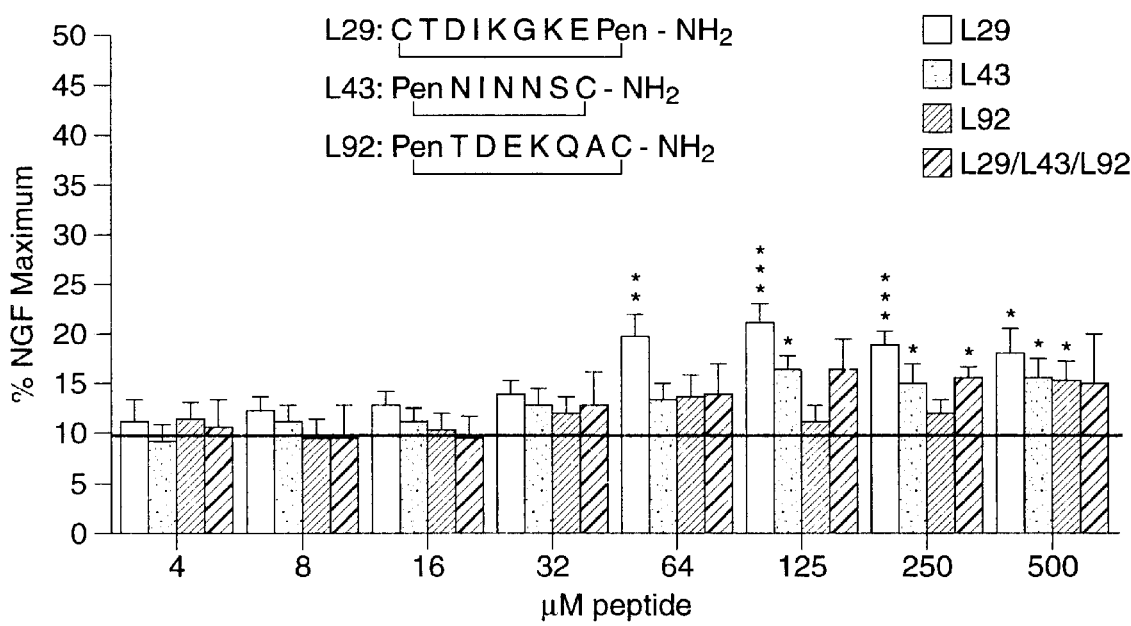
FIG. 2. Neurotrophic activity of NGF loop peptides L29, L43 and L92. Peptides were cyclized by disulfide bond formation between cysteine and penicillamine sulfhydryl groups (indicated by lines). The symbol "Pen" represents penicillamine. The main (largest) HPLC peak from each of the three peptide purifications was tested. A combination of all three peptides was tested such that 500 μM indicates that each peptide was present at 500 μM. The data are an average of six independent bioassays for individual peptides and four bioassays for the combination (±SE). Background survival in the absence of NGF or peptide was 9.7±4% (S.D.) of maximum NGF-supported survival. Survival promoted by peptides L29, L43 and L92 was significantly above background at the indicated concentrations (*, $p<0.05$; , $p,0.01$; *, $p<0.001$; student t test, two-tailed test).

Peptides were cyclized by disulfide bond formation between cysteine and penicillamine sulfhydryl groups (indicated by lines). The location of disulfide bonds was chosen to resemble the location of intra β-hairpin loop hydrogen bonds. The main (largest) HPLC peak from each of the three peptide purifications was tested. The three NGF β-hairpin loop peptides were assayed for their ability to promote neuronal survival by the morphological/MTT assay (FIG. 2). A combination of all three peptides was tested such that 500 $\mu$M indicates that each peptide was present at 500 $\mu$M. Only the main (largest) HPLC peak for each peptide was tested. Peptide L29 had activity significantly above background in the concentration range 64–500 $\mu$M, L43 at 125–500 $\mu$M and L92 at only 500 $\mu$M (significance levels are shown in FIG. 2). When data for each peptide over the concentration range 64 to 500 $\mu$M was combined, L29 had significantly higher activity compared to L43 ($p<0.005$) and L92 ($p<0.0001$; student t test, two-tailed test). The highest activity measured was 20% of the NGF maximum. The combination of all three β-hairpin loop peptides did not demonstrate additive or synergistic activity; instead, the combination resulted in trophic activity lower than obtained with L29 alone (FIG. 2). Since L29 had the highest activity, the NGF 29–36 β-hairpin loop region was further characterized.

Example 2

Bioassays of Cyclic Peptides Derived from L29

The NGF 29–36 β-hairpin loop region was further studied by synthesizing a series of ten cyclized peptides corresponding to this region and incorporating a variable number of residues within the ring structure (FIG. 3). Ten cyclized/oxidized peptides with varying numbers of residues incorporated into the ring structure were purified and multiple HPLC fractions from each peptide assayed by the automated MTT method. Peptide L29 contained 9 residues within its ring structure; therefore, peptides in this series were designed to contain from 7 to 11 residues in the ring structure. Five peptides were synthesized with penicillamine at the N-terminus and cysteine at the amide terminus (P7 through P11, incorporating 7 through 11 residues in the ring structure, compared to 9 residues in peptide L29 ). Five peptides with the same sequence except with the arrangement of the penicillamine and cysteine residues reversed (7P through 11P) were also tested.

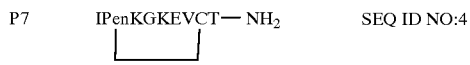

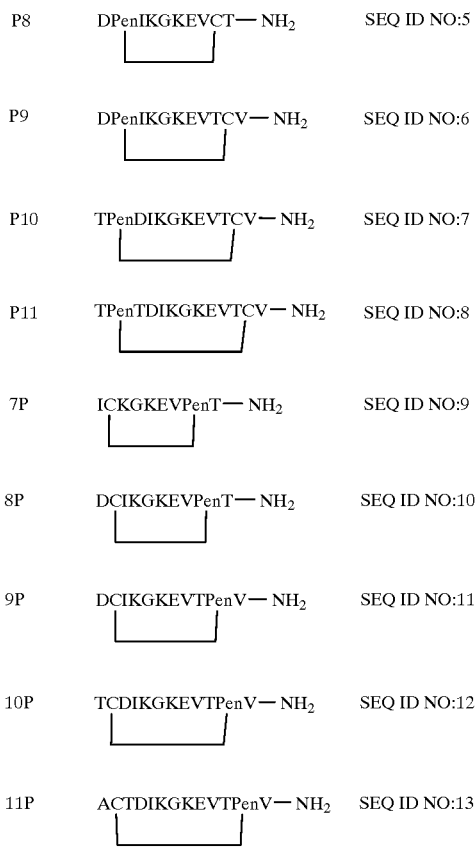

Each peptide, except for peptide 9P, eluted in multiple HPLC fractions, each of which were assayed. Peptides P7, 7P and P9 had the highest activity at the lowest concentrations. Automated MTT bioassays of the ten peptides from this region showed three primary findings (FIG. 3). First, three peptides tended to be more potent in promoting neuronal survival than the others (P7, 7P and P9 ). Overall, peptide P7 had the greatest survival-promoting activity at the lowest concentration. Second, the location of the penicillamine moiety near the N-terminus (peptides P7–P11) instead of the amide terminus (7P–11P) resulted in significantly higher values of % NGF maximum activity ($P<0.05$; paired student $\tau$ test; five values derived from the P7–P11 category compared to five values from the 7P–11P category). In contrast, the location of the penicillamine moiety did not appear to influence the concentrations (potency) at which maximum activities were observed. Third, in most cases, peptides in later eluting fractions had greater activity per $\mu$mole of peptide while peptides in the main peak had less activity. Quantitative amino acid analysis demonstrated that all HPLC fractions contained peptide with the correct number of amino acid residues and were without detectable fractions of truncated peptides or peptides with deletions.

Example 3

Bioassays of peptide P7

Peptide P7, (IPenKGKEVCT), (SEQ ID NO:4) was used to further establish the relationship between structure and bioactivity. Three additional syntheses of P7 were performed. In addition, a control peptide with the identical residues in a scrambled order was also synthesized:

P7 scrambled: IPenKEGKVCT—NH₂  SEQ ID NO:14

In this scrambled sequence the basic side chains of the lysine groups were separated by both glycine and glutamic acid residues instead of only by glycine as in P7. All HPLC fractions (shown in FIG. 4C) were assayed. The bioactivity of three forms of P7 (linear non-oxidized, cyclized/oxidized and scrambled-cyclized/oxidized) were compared using the morphological/MTT assay. Upon addition of MTT to cell cultures, linear P7 peptide, but not cyclized/oxidized peptides, caused the culture medium to immediately turn blue. This process likely reflected the presence of reduced sulfhydryl moieties in linear P7 and the availability of protons for reduction of MTT. The automated MTT assay was therefore not useful for measuring survival-promoting activity of linear P7 peptides. The absence of this phenomenon with cyclized/oxidized peptides process further confirmed that cyclized/oxidized peptides contained stable, oxidized intra- or intermolecular disulfide bonds as a result of the oxidation process. The absence of detectable free sulfhydryl groups in HPLC fractions containing peptide dimers/multimers indicated that the dimers are present in a cyclized rather than a linear polymeric state.

Figures 4A, 4B:
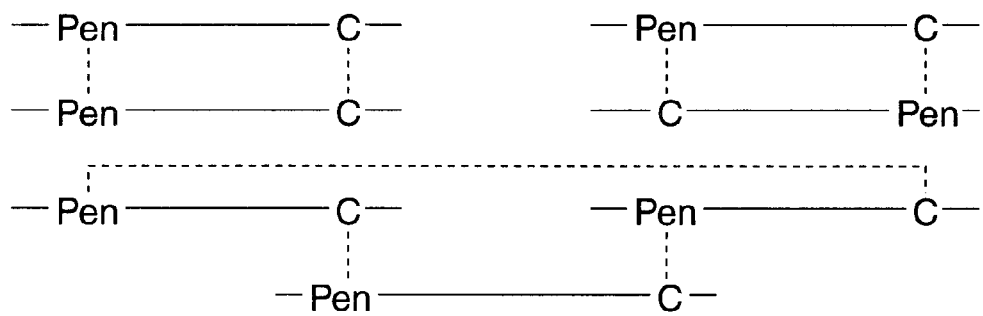
FIG. 4. Peptide P7 structure variants and HPLC purification. A. Peptide P7 with side chain protecting groups and their molecular weights. The predicted mass of P7 without protecting groups is 1007; with all protecting groups present is 1873. B. Examples of potential cyclic peptide multimers formed after P7 oxidation. C. HPLC purification of P7 cyclic, P7 scrambled and P7 linear and corresponding mass spectral data for HPLC subfractions. Crude P7 peptide was loaded onto a C-18 reversed phase column and eluted with a linear gradient of acetonitrile as described in Methods. P7 cyclized/oxidized and linear peptide preparations were derived from the same synthesis, a portion of which was used for cyclization/oxidation. Eluate was collected in six fractions at the times (in minutes) indicated with the main (largest) peak was eluting in the first fraction. For each HPLC fraction the predominant peaks derived from each fraction by MALDI mass spectrometry are listed. Mass values of 2012 or more are consistent with peptide multimers. Fractions supporting >50% of the NGF maximum for neuronal survival (see FIG. 5) are indicated with an asterix.
Figure 4C:
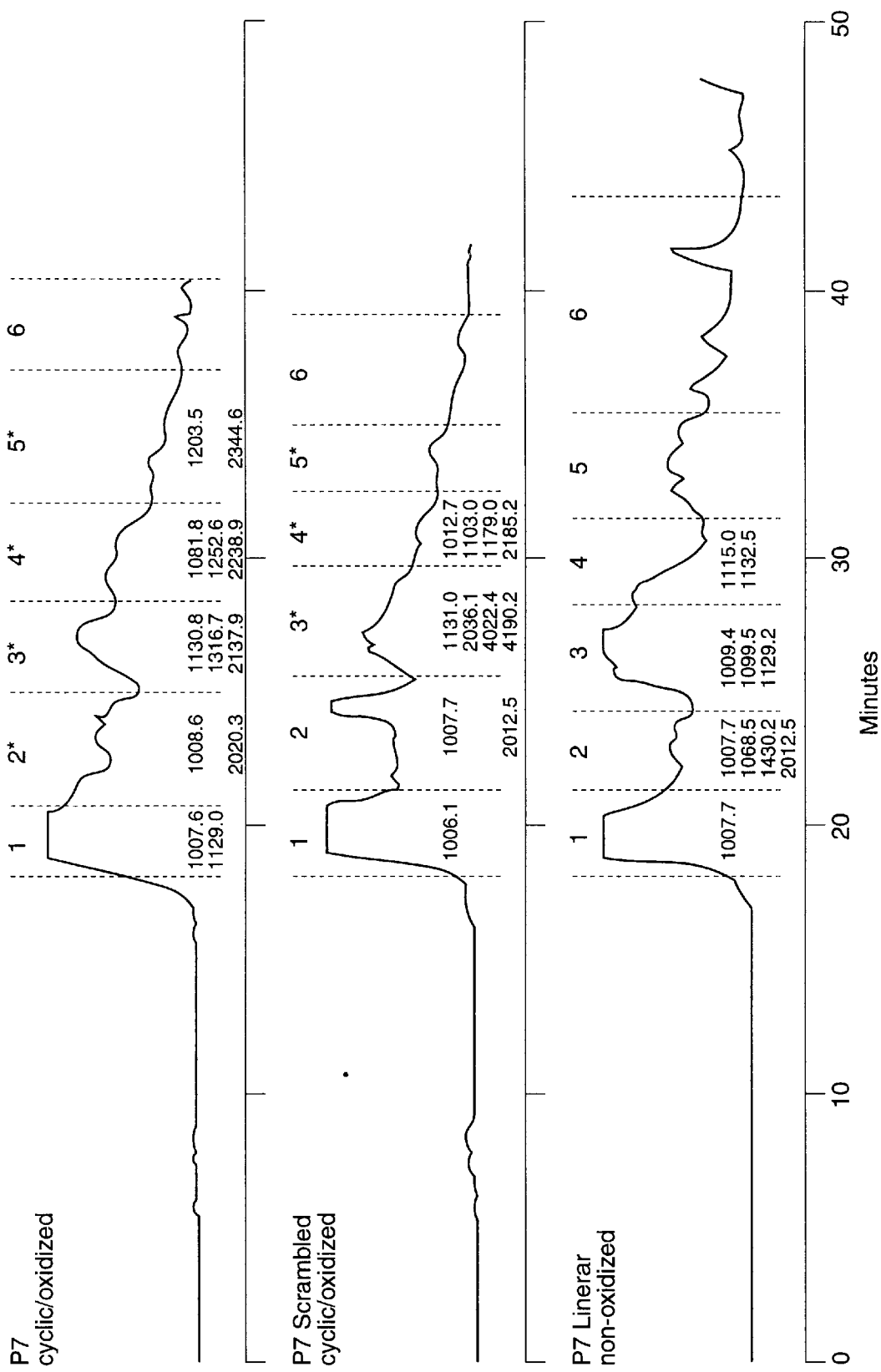
Figure 5:
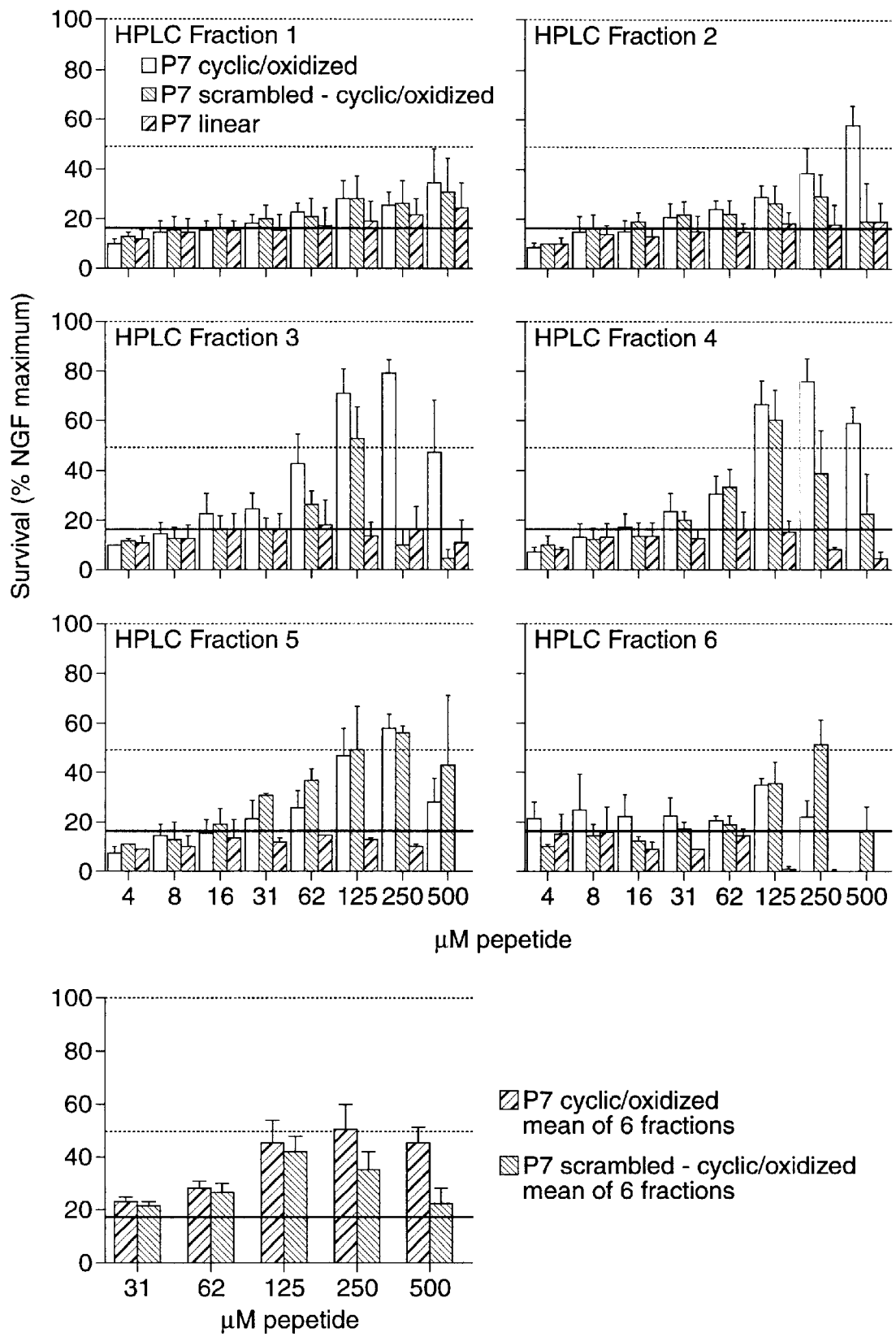
FIG. 5. comparison of neurotrophic activity of cyclized/oxidized peptide P7 (P7 cyclic), a peptide containing the same residues in a scrambled order (P7 cyclic-scrambled) and linear P7 as determined by morphological/MTT bioassay. Each peptide preparation was purified and collected into six HPLC fractions as shown in FIG. 4. Each value is the average derived from four independent bioassays (±SE); the value from each bioassay was an average from duplicate wells. Lower Panel: For each peptide concentration the mean value (±SE) derived from all six HPLC fractions is shown.

The bioactivity of individual HPLC fractions of the three forms of peptide P7 was measured using the morphological/MTT assay (FIGS. 4 and 5). Each peptide preparation was purified and collected into six HPLC fractions as shown in FIG. 4. Fractions were assayed over the indicated concentration range shown in FIG. 5. Sequence specificity of P7 activity was investigated by comparing bioactivity of P7 and P7-scrambled (FIG. 5). For each HPLC fraction, P7 and P7-scrambled activities at each peptide concentration were compared to each other by repeated measures ANOVA. Both P7 and P7 scrambled peptides showed activity. In HPLC fractions 2, 3 and 4, P7 peptides had significantly greater activity than P7-scrambled peptides with the following levels of significance: fraction 2, P=0.054; fraction 3, P=0.0003; fraction 4, P=0.019. In fractions 1, 5 and 6 peptides P7 and P7-scrambled had similar levels of activity. Overall, when the value from all 6 HPLC fractions at each concentration of peptide were compared by repeated measures ANOVA, P7 peptides had significantly greater activity than P7-scrambled peptides (P=0.023). While these assays suggested that the order of the amino acid sequence might also influence activity, the observation that peptides with scrambled sequence had considerable activity indicated that a significant part of the survival-promoting activity was not entirely dependent on an absolutely conserved structure.

Three consistent relationships between peptide preparation and activity were found. First, cyclized/oxidized peptides had considerable activity while no significant activity of linear non-oxidized P7 peptides was detected, suggesting that the presence of a disulfide bond either via cyclization or formation of peptide multimers was necessary for peptide activity. Second, as observed with the ten peptides tested above, P7 and P7-scrambled peptides in late-eluting fractions had greater activity on a molar basis while peptides in the main peak had less activity. Quantitative amino acid analysis again demonstrated that all HPLC fractions contained peptide with the correct number of amino acid residues.

Peptide support of neuronal survival and neurite outgrowth

Figure 6:
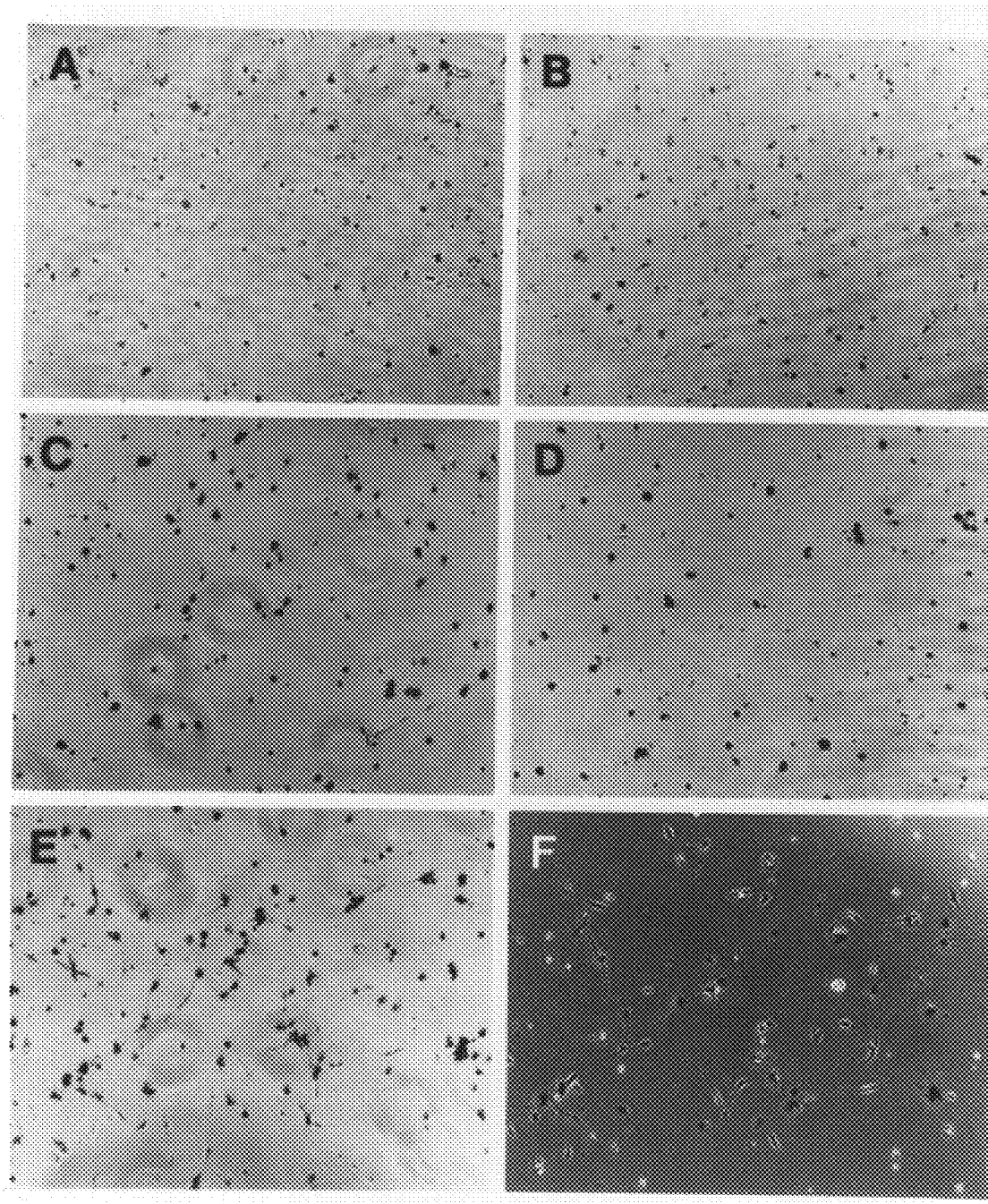
FIG. 6. Phase contrast microscopy of living cultures 8 hours following addition of MTT. Large and intact cells, filled with blue product are counted as surviving. A. Background survival without NGF or peptide; B. P7-linear, HPLC fraction 2 at 250 $\mu$M resulted in survival similar to background; C. P7-cyclized, HPLC fraction 4 at 250 $\mu$M; D. P7-scrambled-cyclized, HPLC fraction 3 at 125 $\mu$M; E. NGF at 800 pg/ml; F. NGF at 800 pg/ml, culture fixed with glutaraldehyde prior to photography.

The appearance of neurons supported by P7 peptides and NGF are shown in FIG. 6. The morphology of neurons supported by NGF and peptides was similar except that in more than 90% of assays, peptide-supported neurons had no neurites. In all assays, control cultures with NGF demonstrated that culture conditions were permissive for neurite outgrowth. This phenomenon was further characterized by determining if peptide-supported cells were still capable of extending processes. After 24 hours in culture, culture medium with P7 peptides was removed and replaced with medium containing NGF at a concentration supporting maximum effect (800 pg/ml). Control cultures supported by NGF during the first 24 hours were similarly processed. After an additional 24 hours cultures were fixed with glutaraldehyde and examined. Cultures originally supported by NGF demonstrated typical neurite outgrowth while peptide-supported cells continued to lack neurites. The absence of neurites indicated that peptide-supported cells had lost their ability to respond to the complete neurotrophic effect of NGF.

Example 4

Bioassays of Subfractions of P7 and P9

The relationship between disulfide formation, multimer formation and/or the presence of persistent side chain protecting groups and NGF agonist activity was further characterized. As shown in FIG. 4C, each HPLC fraction contained multiple peptide species; therefore, it was possible that some species were inactive while others were considerably more potent. MALDI mass spectroscopy of late-eluting peptide fractions (FIG. 4C) demonstrated complex spectra characteristic of incomplete removal of protecting groups and/or side reactions such as internal cyclization or multimer formation. The absence of detectable sulfhydryl groups in oxidized peptide preparations indicated that all of the oxidized fractions contained peptides with the similar number of disulfide bonds on a molar basis. Given the large differences in activity across different fractions, it was unlikely that the presence of disulfide bonds per se was sufficient to render peptides active. It was of particular interest to note; however, that across HPLC fractions, the presence of peptide multimers was significantly correlated with those fractions demonstrating the highest levels (>50% of NGF maximum effect) of bioactivity (Fisher's exact test, two-sided P value=0.02). As described below, further purification of the HPLC fractions gave pure subfractions of homogenous material whose structure could be assigned by mass spectrometry as the cyclic disulfide linked dimers of the parent peptide.

Figure 7:
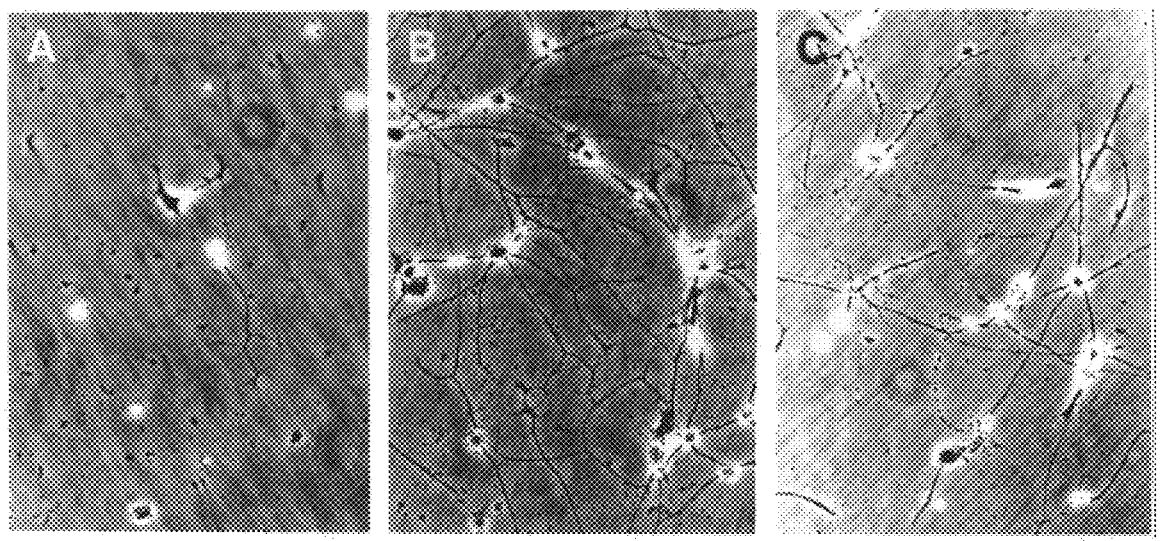
FIG. 7. Neurite promoting effect of peptide P9. Cultures were fixed at 24 hours, no MTT was added. A. Without NGF or peptide; B. NGF at 800 pg/ml; C. Peptide P9 cyclic-oxidized (HPLC fraction 5, subfraction c) at 32 $\mu$M.

Late-eluting fractions of P7 and P9 were subfractionated by reapplication to the reversed phase column and eluted into smaller subfractions. Quantitative amino acid analysis of each subfraction demonstrated the presence of the predicted peptide and did not detect truncated or deleted peptides. For both P7 and P9, subfractions were obtained which supported both neuronal survival and neurite outgrowth (P7 shown in FIG. 7). The data showed that subfractions of peptides P7 and P9 promoted neurite outgrowth. At optimal concentrations of peptide (25–50 μM), survival and neurite promoting activity of each subfraction were both approximately 60% of the maximum NGF effect. The morphology of neurons supported by NGF at a half-maximum concentration and by peptides at an optimal concentrations were not distinguishable. P7 and P9 subfractions eluted with different retention times indicating that the active components of each subfraction were likely to be intrinsic to the peptides themselves rather than non-peptide co-purifying entities. Three out of four separate syntheses of P7 and three out of four separate syntheses of P9 demonstrated neurite-promoting activity in a small number of subfractions. This activity was present in less than 10% of P7 and P9 subfraction containing survival-promoting activity; thus the neurite-promoting activity of peptides was not nearly as consistent or robust as the survival-promoting activity.

Figure 10:
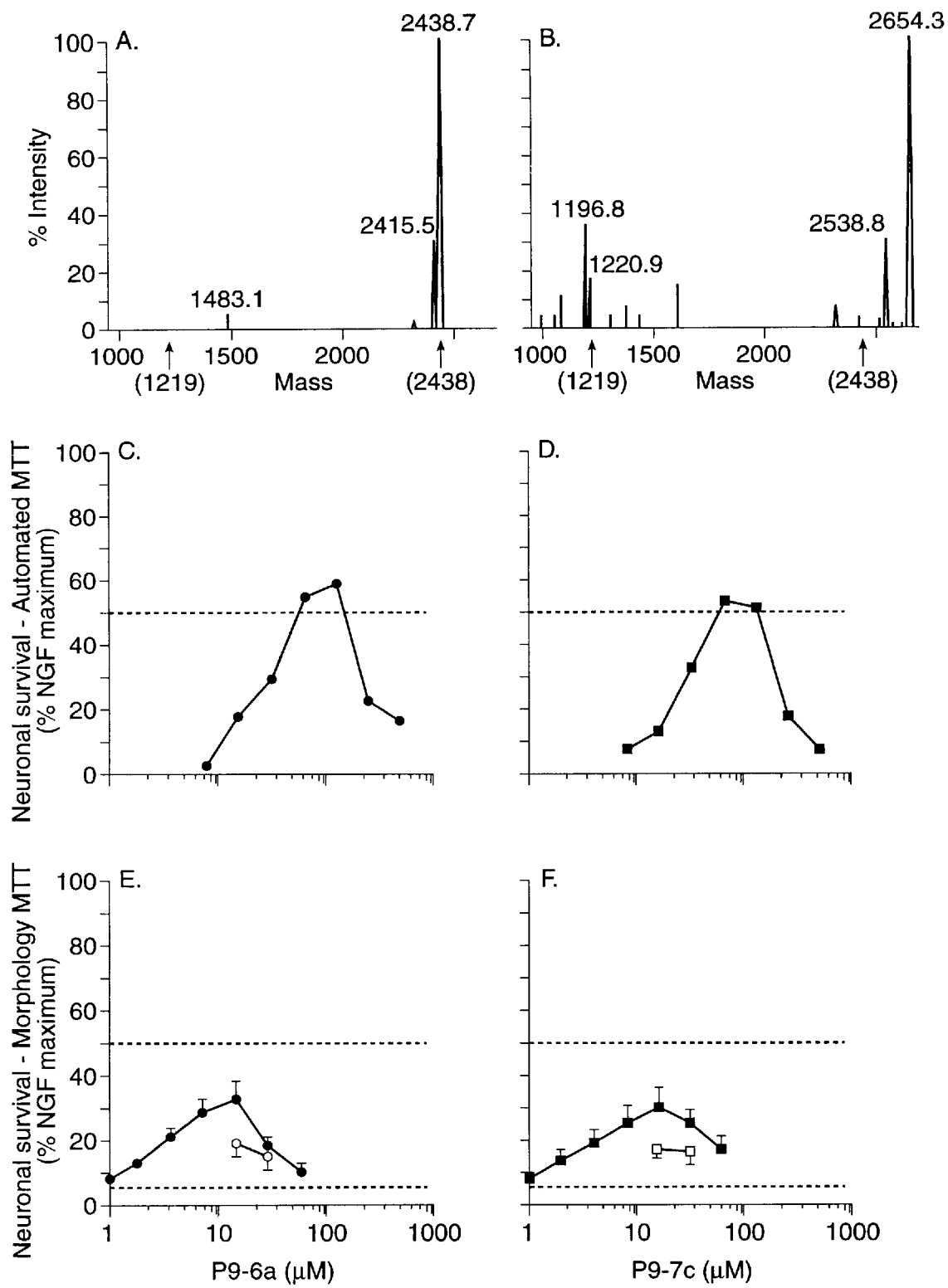
FIG. 10. Mass spectral analysis of a purified P9 subfraction showing presence of a single pure dimer. Survival promoting activity of pure peptide cyclic diner subfractions. Subfraction P9 -6a was the mid-portion of the peak generated by re-application of fraction P9 -6. Subfraction P9 -7c was the third of 6 subpeaks generated by re-application of fraction P9 -7. A. On mass spectrometry of P9 -6a no monomer of the expected mass of 1219 was detected; the predominant species was a dimer with the expected mass of 2438. B. Analysis of P9 -7c showing some monomer with mass 1219, but predominant species of mass 2654 suggesting the dimer with 2 persisting bzl side chain protecting groups of mass 108 each. C, D. Assay of subfractions P9 -6a and P9 -7c by the automated MTT method demonstrating activity of similar potency in the 10–100 $\mu$M range. Each value is the average of duplicate microwell optical density reading. Background survival of ≈10% was subtracted during optical density reading. Decreased activity at higher concentrations was consistently noted. E, F. Assay of subfractions P9 -6a and P9 -7c by the morphological/MTT method demonstrating activity near similar concentrations, though a lower NGF max. was reached (closed symbols; mean ± SE, n=5 assays). Addition of p75 antiserum (open symbols, n=4 assays) inhibited activity by ≈50%. Background survival is indicated at a mean of 6% for this group of assays.

A P9 peptide preparation was further subfractionated and reanalyzed by MALDI mass spectrometry. Unlike the parent HPLC fractions, these subfractions showed the presence of a single species by MALDI mass spectrometry of molecular weight 2438 (FIG. 10), twice the molecular weight of the P9 monomer. This demonstrates the absence of side chain protecting groups. Since this P9 subfraction had previously been shown to lack free sulfhydryl groups by the MTT test, the structure of the peptide in this P9 subfraction has been assigned as the bis-disulfide linked cyclic dimer. Biological activity of this P9 dimer is shown in FIG. 10 and demonstrates that pure peptide cyclic dimer subfractions retain survival-promoting activity.

HPLC subfractions were prepared from P7 and P9 fractions previously shown to contain survival promoting activity. Several P9 subfractions having the highest activity (approx. 50% of NGF max.) at the lowest concentrations (50–100 $\mu$M) were further characterized. Subfraction P9-6a was the midportion of the peak generated by reapplication of fraction P9-6. Subfraction P9-7c was the 3rd of 6 subpeaks generated by reapplication of fraction P9-7. As shown in FIG. 10, subfraction P9-6 A contained no detectable monomeric peptide; instead the predominant species was a dimer of the expected mass of 2438. Analysis of P9-7c detected some monomer but also largely consisted of dimer with a mass of 2654 indicating the additional presence of 2 persisting bzl side chain protecting groups with a mass of 108 each. Using the automated MTT method, both subfractions had equipotent activity in the 10–100 $\mu$M range showing that the side chain protecting groups were not required for activity (FIG. 10). Bioassay of subfractions by the morphological/MTT method demonstrated activity near a similar concentration although a lower % NGF maximum was reached (FIG. 10). For both types of assays, decreased activity at higher concentrations was consistently noted. As demonstrated for P7 fractions, addition of p75 antiserum inhibited activity by approx. 50% These observations confirmed that peptide dimerization (formed by interpeptide cyclization), not necessarily the presence of side chain protecting groups led to increased activity.

Figure 8A:
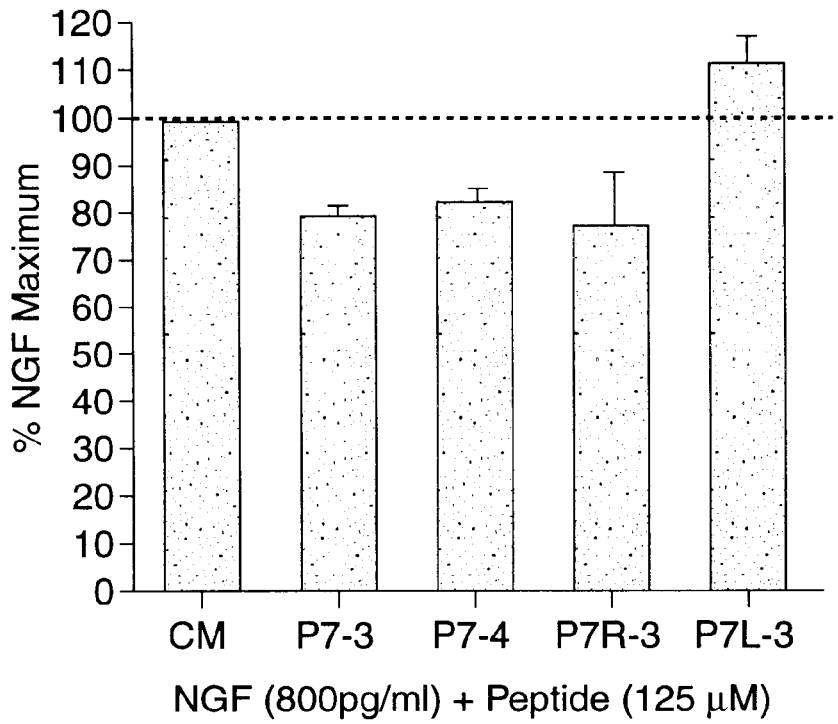
FIG. 8. P7 peptides inhibit NGF but are not inhibited by K252a. A. Peptides at a concentration of 125 GmM were assayed in the presence of NGF at 800 pg/ml which supported maximum survival. The morphological/MTT assay was used. Peptides P7-3 and P7-4 significantly inhibited the NGF survival-promoting effect by approximately 20% (P<0.01, Wilcoxon signed rank test; n=8, ±SE). P7-3-Scrambled also inhibited NGF by a similar degree but with more variability (n=6). Linear P7-3 had no inhibitory effect (n=6). B. K252a (100 $\mu$M) inhibited NGF (800 pg/ml) by approximately 50% but had no detectable inhibitory effect on P7-3 and P7-4 tested at 125 $\mu$M in the same assays.
Figure 8B:
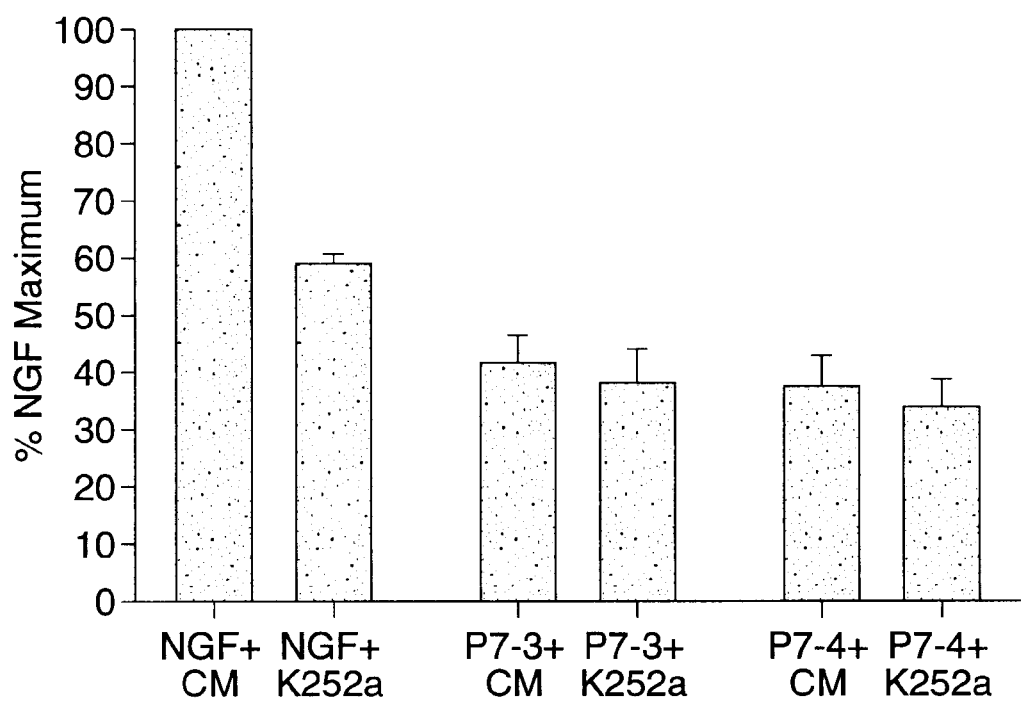

Several agents which have NGF-like activity have demonstrated additive effects even when added to NGF levels supporting maximum neurotrophic response. Additivity between NGF at plateau concentrations and the most potent fraction of P7 would support the possibility that P7 peptides function via mechanisms other than agonist-like NGF receptor-ligand interaction. Peptide P7-fraction-3 and P7-fraction-4 at 125 $\mu$M had ~80% of the NGF maximum survival-promoting effect when tested alone (FIG. 5). The combination of P7-fraction-3 or P7-fraction-4 at 125 $\mu$M and NGF at 800 pg/ml (at the plateau of the NGF dose-response curve) was tested using the same MTT/morphology assay (FIG. 8). The data showed that peptide and maximum NGF neurotrophic activities were not additive. Instead of additivity, the addition of P7-3 or P7-4 to NGF resulted in a significant inhibition of NGF effect to 79.8±1.8% (P7-3) and 82.5±1.3% (P7-4) of the NGF maximum (mean of 8 bioassays each, ± SE, data from 4 wells averaged for each of bioassay; P<0.01, Wilcoxon signed rank test for both peptides). P7-3 scrambled also inhibited NGF to a similar degree but with more variability than while linear P7-3 had no inhibitory effect. These findings indicate that cyclization increased the inhibitory properties of the peptides. In assays in which the the Trk kinase inhibitor K252A blocked NGF activity by 50%, no inhibition of P7-3 or P7-4 was detected (FIG. 8), indicating that the peptides do not require Trk kinase activity.

Example 5

Bioassays with p75 antiserum

Antiserum (antibody 9651) directed against the third and fourth cysteine rich repeats of the extracellular domain of mouse p75 was obtained as described in Huber (infra). The 9651 rabbit polyclonal antisera against the mouse P75 receptor was generated against a bacterial fusion protein consisting of glutathione-S-transferase (GST) sequences linked to amino acids 43–161 (according to Johnson et al, *Cell*, 47:545–554 (1986) from the mouse P75 neurotrophin receptor. This extracellular receptor domain is involved in NGF binding. This antibody inhibits NGF neurotrophic activity by interfering with NGF-p75 interaction (Huber et al, "A potential interaction of p75 and trkA NGF receptors revealed by affinity crosslinking and immunoprecipitation", *J. Neurosci. Res.*, 40:557–563 (1995)). Antiserum and control non-immune serum were tested at final dilutions of 1:100 in the presence of NGF or peptide.

Figure 9:
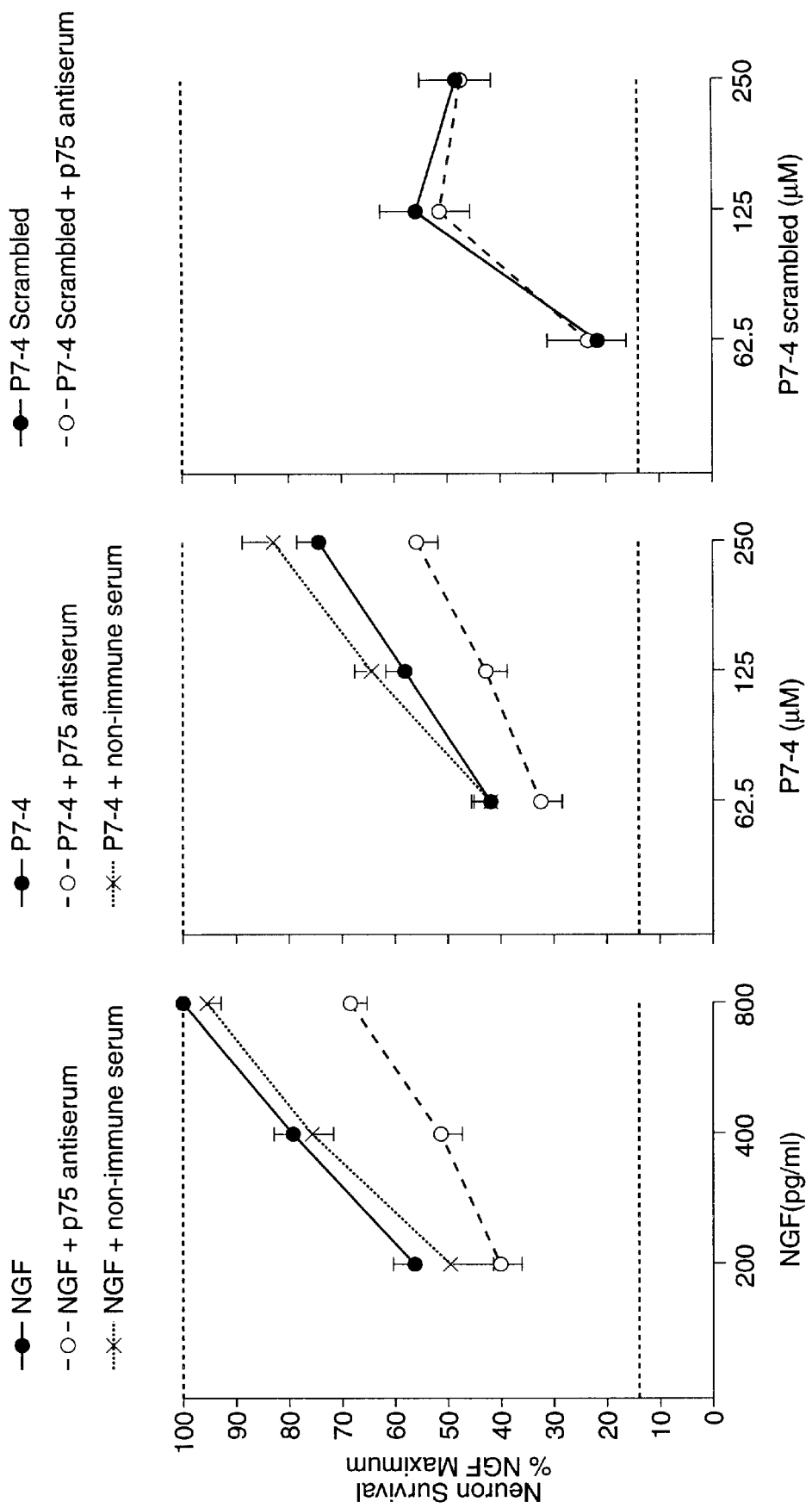
FIG. 9. Antibody to the NGF p75 receptor inhibits the survival-promoting effect of P7-4. NGF and peptides P7-4 (cyclic-oxidized) and P7-4-scrambled (cyclic-oxidized) were assayed for survival-promoting activity using the morphological/MTT assay. Values indicate mean ± SE derived from the follwing number of bioassays: NGF ± antiserum n=10; NGF+ non-immune serum n=6; P7-4 antiserum n=8; P7-4+ non-immune serum n=4; P7-4-scrambled ± antiserum n=5. Non-immune serum (1:100 final dilution) had little effect while p75 antiserum (1:100 final dilution) inhibited NGF by an average of 40% over the three concentrations tested. P75 antiserum inhibited P7-4 by an average of 32% over the three concentrations tested (P<0.0005 repeated measures ANOVA). p75 antiserum had no detectable effect on the bioactivity of P7-4-Scrambled.

To determine if activity of P7 and P7-scrambled peptides was dependent on p75, their activity in the presence of p75 antiserum (1:100 final dilution) which inhibits NGF neurotrophic activity was measured. Under the assay conditions of this study, p75 antiserum in the absence of NGF or peptides had no detectable effect on neuronal survival. In 15 bioassays, control background survival was 14±2% (S.E.) of the NGF maximum compared to a background in the presence of p75 antiserum of 13±2% in 5 of the same 15 assays. As shown in FIG. 9, p75 antiserum inhibited NGF by an average of 40% over the three NGF concentrations tested. Non-immune serum had little effect. p75 antiserum had a highly significant inhibitory effect on P7-4 peptides by an average of 32% over the three concentrations tested (P<0.00005; repeated measures ANOVA). p75 antiserum had no detectable effect on the bioactivity of P7-Scrambled-fraction-4 peptides. The data showed that antiserum directed against the NGF p75 receptor inhibited P7 bioactivity.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound displaying nerve growth factor (NGF) agonist or partial agonist activity, wherein the compound is a cyclic dimer consisting of a sequence of amino acid residues 43–47 of NGF (SEQ ID NO:2) or amino acid residues 92–97 of NGF (SEQ ID NO:3) or biologically functional equivalents thereof, wherein the sequence consists of penicillamine residue and a cysteine residue at the termini and the cyclic dimer is formed by disulfide bridges between the penicillamine and cysteine residues.

2. The compound of claim 1, wherein the NGF is of mammalian origin.

3. The compound of claim 1, wherein the NGF is of human origin.

4. The compound of claim 1, wherein the sequence of amino acids is residues 43–47 of NGF (SEQ ID NO:2).

5. The compound of claim 1, wherein the sequence of amino acids is residues 92–97 of NGF (SEQ ID NO:3).

6. The compound of claim 1, wherein the dimer is a homodimer.

7. A pharmaceutical composition comprising a therapeutically effective amount of the NGF agonist or partial agonist of claim 1 and a pharmaceutically acceptable excipient.

8. A pharmaceutical composition comprising a therapeutically effective amount of the NGF agonist or partial agonist of claim 2 or 3 and a pharmaceutically acceptable excipient.

9. A pharmaceutical composition comprising a therapeutically effective amount of the NGF agonist or partial agonist of claim 4 or 5 and a pharmaceutically acceptable excipient.

10. A method of treatment of a neutodegenerative disorder which method comprises treating an individual suffering from such disorder by adminiistering a therapeutically effective amount of the NGF agonist of claim 1.

11. A method of treatment of a neurodegenerative disorder which method comprises treating an individual suffering from such disorder by administering a therapeutically effective amount of the NGF agonist of claims 2 or 3.

12. A method of treatment of a neurodegenerative disorder which method comprises treating an individual suffering from such disorder by administering a therapeutically effective amount of the NGF agonist of claims 4 or 5.

13. The method of claim 11 wherein the disorder is a neurodegenerative disorder of the central nervous system.

14. The method of claim 13, wherein the neurodegenerative disorder is Alzheimer's disease, amyotrophic lateral sclerosis (ALS), neuropathies, neural injury secondary to hypoxia, ischemia or trauma, process involving apoptosis, or Huntington's disease.

* * * * *

UNITED STATES PATENT AND TRADEMARK OFFICE
CERTIFICATE OF CORRECTION

PATENT NO. : 5,958,875
DATED : September 28, 1999
INVENTOR(S) : Frank M. Longo, et. al.

It is certified that error appears in the above-identified patent and that said Letters Patent is hereby corrected as shown below:

Column 1, line 9, insert --
This invention was made with Government support under Grant Nos. NS16349 and NS25011, awarded by the National Institutes of Health and the Department of Veteran Affairs. The Government has certain rights in this invention.--

Signed and Sealed this

Third Day of October, 2000

*Attest:*

Q. TODD DICKINSON

*Attesting Officer*  *Director of Patents and Trademarks*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
         (A) LENGTH: 9 amino acids
         (B) TYPE: amino acid
         (C) STRANDEDNESS: single
         (D) TOPOLOGY: both (ii) MOLECULE TYPE: peptide (ix) FEATURE:
         (A) NAME/KEY: Disulfide-bond
         (B) LOCATION: 1..9

(ix) FEATURE:
         (A) NAME/KEY: Region
         (B) LOCATION: one-of(9)
         (D) OTHER INFORMATION: /note= "Xaa is penicillamine."

(xi) SEQUENCE DESCRIPTION: SEQ ID NO:1:

Cys Thr Asp Ile Lys Gly Lys Glu Xaa
1               5

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS: single
         (D) TOPOLOGY: both (ii) MOLECULE TYPE: peptide (ix) FEATURE:
         (A) NAME/KEY: Disulfide-bond
         (B) LOCATION: 1..7

(ix) FEATURE:
         (A) NAME/KEY: Region
         (B) LOCATION: one-of(1)
         (D) OTHER INFORMATION: /note= "Xaa is penicillamine."

(xi) SEQUENCE DESCRIPTION: SEQ ID NO:2:

Xaa Asn Asn Ile Asn Ser Cys
1               5

(2) INFORMATION FOR SEQ ID NO:3:

(i) SEQUENCE CHARACTERISTICS:
         (A) LENGTH: 8 amino acids
         (B) TYPE: amino acid
         (C) STRANDEDNESS: single
         (D) TOPOLOGY: both (ii) MOLECULE TYPE: peptide (ix) FEATURE:
         (A) NAME/KEY: Disulfide-bond
         (B) LOCATION: 1..8

(ix) FEATURE:
         (A) NAME/KEY: Region
         (B) LOCATION: one-of(1)
         (D) OTHER INFORMATION: /note= "Xaa is penicillamine."

(xi) SEQUENCE DESCRIPTION: SEQ ID NO:3:

Xaa Thr Asp Glu Lys Gln Ala Cys (2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: both
        (D) TOPOLOGY: both (ii) MOLECULE TYPE: peptide (ix) FEATURE:
        (A) NAME/KEY: Cross-links
        (B) LOCATION: one-of(2, 8)
        (D) OTHER INFORMATION: /note= "Positions 2 and 8 may be
            involved in homodimeric or heterodimeric
            crosslinks."

(ix) FEATURE:
        (A) NAME/KEY: Region
        (B) LOCATION: one-of(2)
        (D) OTHER INFORMATION: /note= "Xaa is penicillamine."

(ix) FEATURE:
        (A) NAME/KEY: Region
        (B) LOCATION: one-of(9)
        (D) OTHER INFORMATION: /note= "C-terminal thr is amidated."

(xi) SEQUENCE DESCRIPTION: SEQ ID NO:4:

```
Ile Xaa Lys Gly Lys Glu Val Cys Thr
1               5
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: both
        (D) TOPOLOGY: both (ii) MOLECULE TYPE: peptide (ix) FEATURE:
        (A) NAME/KEY: Cross-links
        (B) LOCATION: one-of(2, 9)
        (D) OTHER INFORMATION: /note= "Positions 2 and 9 may be
            involved in homodimeric or heterodimeric
            crosslinks."

(ix) FEATURE:
        (A) NAME/KEY: Region
        (B) LOCATION: one-of(2)
        (D) OTHER INFORMATION: /note= "Xaa is penicillamine."

(ix) FEATURE:
        (A) NAME/KEY: Region
        (B) LOCATION: one-of(10)
        (D) OTHER INFORMATION: /note= "C-terminal thr is amidated."

(xi) SEQUENCE DESCRIPTION: SEQ ID NO:5:

```
Asp Xaa Ile Lys Gly Lys Glu Val Cys Thr
1               5                   10
```

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: both
        (D) TOPOLOGY: both (ii) MOLECULE TYPE: peptide (ix) FEATURE:

```
            (A) NAME/KEY: Cross-links
            (B) LOCATION: one-of(2, 10)
            (D) OTHER INFORMATION: /note= "Positions 2 and 10 may be
                involved in homodimeric or heterodimeric
                crosslinks."

(ix) FEATURE:
            (A) NAME/KEY: Region
            (B) LOCATION: one-of(2)
            (D) OTHER INFORMATION: /note= "Xaa is penicillamine."

(ix) FEATURE:
            (A) NAME/KEY: Region
            (B) LOCATION: one-of(11)
            (D) OTHER INFORMATION: /note= "C-terminal val is amidated."

(xi) SEQUENCE DESCRIPTION: SEQ ID NO:6:

Asp Xaa Ile Lys Gly Lys Glu Val Thr Cys Val
1               5                   10

(2) INFORMATION FOR SEQ ID NO:7:

(i) SEQUENCE CHARACTERISTICS:
            (A) LENGTH: 12 amino acids
            (B) TYPE: amino acid
            (C) STRANDEDNESS: both
            (D) TOPOLOGY: both (ii) MOLECULE TYPE: peptide (ix) FEATURE:
            (A) NAME/KEY: Cross-links
            (B) LOCATION: one-of(2, 11)
            (D) OTHER INFORMATION: /note= "Positions 2 and 11 may be
                 involved in homodimeric or heterodimeric crosslinks."

(ix) FEATURE:
            (A) NAME/KEY: Region
            (B) LOCATION: one-of(11)
            (D) OTHER INFORMATION: /note= "Xaa is penicillamine."

(ix) FEATURE:
            (A) NAME/KEY: Region
            (B) LOCATION: one-of(2)
            (D) OTHER INFORMATION: /note= "Xaa is penicillamine."

(ix) FEATURE:
            (A) NAME/KEY: Region
            (B) LOCATION: one-of(12)
            (D) OTHER INFORMATION: /note= "C-terminal val is amidated."

(xi) SEQUENCE DESCRIPTION: SEQ ID NO:7:

Thr Xaa Asp Ile Lys Gly Lys Glu Val Thr Cys Val
1               5                   10

(2) INFORMATION FOR SEQ ID NO:8:

(i) SEQUENCE CHARACTERISTICS:
            (A) LENGTH: 13 amino acids
            (B) TYPE: amino acid
            (C) STRANDEDNESS: both
            (D) TOPOLOGY: both (ii) MOLECULE TYPE: peptide (ix) FEATURE:
            (A) NAME/KEY: Cross-links
            (B) LOCATION: one-of(2, 12)
            (D) OTHER INFORMATION: /note= "Positions 2 and 12 may be
                 involved in homodimeric or heterodimeric crosslinks."

(ix) FEATURE:
            (A) NAME/KEY: Region
            (B) LOCATION: one-of(2)
            (D) OTHER INFORMATION: /note= "Xaa is penicillamine."
```

```
       (ix) FEATURE:
             (A) NAME/KEY: Region
             (B) LOCATION: one-of(13)
             (D) OTHER INFORMATION: /note= "C-terminal val is amidated."

(xi) SEQUENCE DESCRIPTION: SEQ ID NO:8:

Thr Xaa Thr Asp Ile Lys Gly Lys Glu Val Thr Cys Val
1               5                   10

(2) INFORMATION FOR SEQ ID NO:9:

(i) SEQUENCE CHARACTERISTICS:
             (A) LENGTH: 9 amino acids
             (B) TYPE: amino acid
             (C) STRANDEDNESS: both
             (D) TOPOLOGY: both (ii) MOLECULE TYPE: peptide (ix) FEATURE:
             (A) NAME/KEY: Cross-links
             (B) LOCATION: one-of(2, 8)
             (D) OTHER INFORMATION: /note= "Positions 2 and 8 may be
                  involved in homodimeric or heterodimeric crosslinks."

(ix) FEATURE:
             (A) NAME/KEY: Region
             (B) LOCATION: one-of(8)
             (D) OTHER INFORMATION: /note= "Xaa is penicillamine."

(ix) FEATURE:
             (A) NAME/KEY: Region
             (B) LOCATION: one-of(9)
             (D) OTHER INFORMATION: /note= "C-terminal thr is amidated."

(xi) SEQUENCE DESCRIPTION: SEQ ID NO:9:

Ile Cys Lys Gly Lys Glu Val Xaa Thr
1               5

(2) INFORMATION FOR SEQ ID NO:10:

(i) SEQUENCE CHARACTERISTICS:
             (A) LENGTH: 10 amino acids
             (B) TYPE: amino acid
             (C) STRANDEDNESS: both
             (D) TOPOLOGY: both (ii) MOLECULE TYPE: peptide (ix) FEATURE:
             (A) NAME/KEY: Cross-links
             (B) LOCATION: one-of(2, 9)
             (D) OTHER INFORMATION: /note= "Positions 2 and 9 may be
                  involved in homodimeric or heterodimeric crosslinks."

(ix) FEATURE:
             (A) NAME/KEY: Region
             (B) LOCATION: one-of(9)
             (D) OTHER INFORMATION: /note= "Xaa is penicillamine."

(ix) FEATURE:
             (A) NAME/KEY: Region
             (B) LOCATION: one-of(10)
             (D) OTHER INFORMATION: /note= "C-terminal thr is amidated."

(xi) SEQUENCE DESCRIPTION: SEQ ID NO:10:

Asp Cys Ile Lys Gly Lys Glu Val Xaa Thr
1               5                   10

(2) INFORMATION FOR SEQ ID NO:11:

(i) SEQUENCE CHARACTERISTICS:
             (A) LENGTH: 11 amino acids
             (B) TYPE: amino acid
```

```
            (C) STRANDEDNESS: both
            (D) TOPOLOGY: both (ii) MOLECULE TYPE: peptide (ix) FEATURE:
            (A) NAME/KEY: Cross-links
            (B) LOCATION: one-of(2, 10)
            (D) OTHER INFORMATION: /note= "Positions 2 and 10 may be
                involved in homodimeric or heterodimeric crosslinks."

(ix) FEATURE:
            (A) NAME/KEY: Region
            (B) LOCATION: one-of(10)
            (D) OTHER INFORMATION: /note= "Xaa is penicillamine."

(ix) FEATURE:
            (A) NAME/KEY: Region
            (B) LOCATION: one-of(11)
            (D) OTHER INFORMATION: /note= "C-terminal val is amidated."

(xi) SEQUENCE DESCRIPTION: SEQ ID NO:11:

Asp Cys Ile Lys Gly Lys Glu Val Thr Xaa Val
1               5                   10

(2) INFORMATION FOR SEQ ID NO:12:

(i) SEQUENCE CHARACTERISTICS:
            (A) LENGTH: 12 amino acids
            (B) TYPE: amino acid
            (C) STRANDEDNESS: both
            (D) TOPOLOGY: both (ii) MOLECULE TYPE: peptide (ix) FEATURE:
            (A) NAME/KEY: Cross-links
            (B) LOCATION: one-of(2, 11)
            (D) OTHER INFORMATION: /note= "Positions 2 and 11 may be
                involved in homodimeric or heterodimeric crosslinks."

(ix) FEATURE:
            (A) NAME/KEY: Region
            (B) LOCATION: one-of(11)
            (D) OTHER INFORMATION: /note= "Xaa is penicillamine."

(ix) FEATURE:
            (A) NAME/KEY: Region
            (B) LOCATION: one-of(12)
            (D) OTHER INFORMATION: /note= "C-terminal val is amidated."

(xi) SEQUENCE DESCRIPTION: SEQ ID NO:12:

Thr Cys Asp Ile Lys Gly Lys Glu Val Thr Xaa Val
1               5                   10

(2) INFORMATION FOR SEQ ID NO:13:

(i) SEQUENCE CHARACTERISTICS:
            (A) LENGTH: 13 amino acids
            (B) TYPE: amino acid
            (C) STRANDEDNESS: both
            (D) TOPOLOGY: both (ii) MOLECULE TYPE: peptide (ix) FEATURE:
            (A) NAME/KEY: Cross-links
            (B) LOCATION: one-of(2, 12)
            (D) OTHER INFORMATION: /note= "Positions 2 and 12 may be
                involved in homodimeric or heterodimeric crosslinks."

(ix) FEATURE:
            (A) NAME/KEY: Region
            (B) LOCATION: one-of(12)
            (D) OTHER INFORMATION: /note= "Xaa is penicillamine."
```

```
    (ix) FEATURE:
          (A) NAME/KEY: Region
          (B) LOCATION: one-of(13)
          (D) OTHER INFORMATION: /note= "C-terminal val is amidated."

(xi) SEQUENCE DESCRIPTION: SEQ ID NO:13:

Ala Cys Thr Asp Ile Lys Gly Lys Glu Val Thr Xaa Val
1               5                   10

(2) INFORMATION FOR SEQ ID NO:14:

(i) SEQUENCE CHARACTERISTICS:
          (A) LENGTH: 9 amino acids
          (B) TYPE: amino acid
          (C) STRANDEDNESS: both
          (D) TOPOLOGY: both (ii) MOLECULE TYPE: peptide (ix) FEATURE:
          (A) NAME/KEY: Cross-links
          (B) LOCATION: one-of(2, 8)
          (D) OTHER INFORMATION: /note= "Positions 2 and 8 may be
                involved in homodimeric or heterodimeric crosslinks."

(ix) FEATURE:
          (A) NAME/KEY: Region
          (B) LOCATION: one-of(2)
          (D) OTHER INFORMATION: /note= "Xaa is penicillamine."

(ix) FEATURE:
          (A) NAME/KEY: Region
          (B) LOCATION: one-of(9)
          (D) OTHER INFORMATION: /note= "C-terminal thr is amidated."

(xi) SEQUENCE DESCRIPTION: SEQ ID NO:14:

Ile Xaa Lys Glu Gly Lys Val Cys Thr
1               5

(2) INFORMATION FOR SEQ ID NO:15:

(i) SEQUENCE CHARACTERISTICS:
          (A) LENGTH: 5 amino acids
          (B) TYPE: amino acid
          (C) STRANDEDNESS: single
          (D) TOPOLOGY: both (ii) MOLECULE TYPE: peptide (xi) SEQUENCE DESCRIPTION: SEQ ID NO:15:

Lys Gly Lys Glu Val
1               5

(2) INFORMATION FOR SEQ ID NO:16:

(i) SEQUENCE CHARACTERISTICS:
          (A) LENGTH: 4 amino acids
          (B) TYPE: amino acid
          (C) STRANDEDNESS: single
          (D) TOPOLOGY: both (ii) MOLECULE TYPE: peptide (xi) SEQUENCE DESCRIPTION: SEQ ID NO:16:

Arg Gly Asp Xaa
```